(12) United States Patent
Collingwood et al.

(10) Patent No.: US 9,322,036 B2
(45) Date of Patent: *Apr. 26, 2016

(54) METHODS AND COMPOSITIONS FOR INACTIVATING ALPHA 1,6 FUCOSYLTRANSFERASE (FUT8) GENE EXPRESSION

(71) Applicant: Sangamo BioSciences, Inc., Richmond, CA (US)

(72) Inventors: Trevor Collingwood, Richmond, CA (US); Gregory J. Cost, Richmond, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 50 days.

This patent is subject to a terminal disclaimer.

(21) Appl. No.: 14/289,459

(22) Filed: May 28, 2014

(65) Prior Publication Data

US 2014/0273097 A1   Sep. 18, 2014

Related U.S. Application Data

(62) Division of application No. 12/931,265, filed on Jan. 7, 2011, now Pat. No. 8,772,025, which is a division of application No. 12/218,035, filed on Jul. 10, 2008, now Pat. No. 7,919,313.

(60) Provisional application No. 60/959,202, filed on Jul. 12, 2007, provisional application No. 60/993,624, filed on Sep. 13, 2007.

(51) Int. Cl.
| | |
|---|---|
| C07K 14/00 | (2006.01) |
| C07H 17/00 | (2006.01) |
| C12N 15/87 | (2006.01) |
| C07K 14/47 | (2006.01) |
| C12N 9/10 | (2006.01) |
| C07K 16/00 | (2006.01) |
| C12N 15/85 | (2006.01) |
| C12P 21/00 | (2006.01) |

(52) U.S. Cl.
CPC ............ *C12N 15/87* (2013.01); *C07K 14/4703* (2013.01); *C07K 16/00* (2013.01); *C12N 9/1051* (2013.01); *C12N 15/85* (2013.01); *C12P 21/00* (2013.01)

(58) Field of Classification Search
CPC ....................................................... C07H 17/00
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,946,292 B2 | 9/2005 | Kanda et al. | |
| 6,979,539 B2 | 12/2005 | Cox, III et al. | |
| 7,013,219 B2 | 3/2006 | Case et al. | |
| 7,153,949 B2 | 12/2006 | Kim et al. | |
| 7,163,824 B2 | 1/2007 | Cox, III et al. | |
| 2002/0081694 A1 | 6/2002 | Taniguchi et al. | |
| 2003/0108880 A1 | 6/2003 | Rebar et al. | |
| 2003/0232410 A1 | 12/2003 | Liljedahl et al. | |
| 2005/0026157 A1 | 2/2005 | Baltimore | |
| 2005/0064474 A1 | 3/2005 | Urnov et al. | |
| 2005/0208489 A1 | 9/2005 | Carroll | |
| 2006/0063231 A1 | 3/2006 | Li et al. | |
| 2006/0079475 A1 | 4/2006 | Zhang et al. | |
| 2006/0188987 A1 | 8/2006 | Guschan et al. | |

(Continued)

FOREIGN PATENT DOCUMENTS

| | | |
|---|---|---|
| EP | 1331266 A1 | 6/2002 |
| EP | 1676860 A1 | 7/2006 |

(Continued)

OTHER PUBLICATIONS

Ihara, et al., "Crystal Structure of Mammalian Alpha 1, 6-Fucosyltransferase, FUT8," Glycobiology 17(5):455-466 (2007).

Javaud, et al., "Ancestral Exonic Organization of FUT8, The Gene Encoding the Alpha6-Fucosyltransferase, Reveals Successive Peptide Domains Which Suggests a Particular Three-Dimensional Core Structure for the Alpha6-Fucosyltransferase Family," Mol. Biol. Evol. 17(11):1661-1672 (2000).

Liu, et al., "Validated Zinc Finger Protein Designs for All 16 GNN DNA Triplet Targets", The Journal of Biological Chemistry 277(6):3850-3856 (2002).

(Continued)

*Primary Examiner* — Karen Cochrane Carlson
(74) *Attorney, Agent, or Firm* — Pasternak Patent Law; Susan Abrahamson

(57) ABSTRACT

Disclosed herein are methods and compositions for inactivating a FUT8 gene, using fusion proteins comprising a zinc finger protein and a cleavage domain or cleavage half-domain. Polynucleotides encoding said fusion proteins are also provided, as are cells comprising said polynucleotides and fusion proteins.

12 Claims, 10 Drawing Sheets

(56) References Cited

U.S. PATENT DOCUMENTS

| | | |
|---|---|---|
| 2006/0210539 A1 | 9/2006 | Zhang et al. |
| 2007/0134796 A1 | 6/2007 | Holmes et al. |
| 2007/0218528 A1 | 9/2007 | Miller |
| 2008/0015164 A1 | 1/2008 | Collingwood |
| 2008/0131962 A1 | 6/2008 | Miller |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | 0023464 A2 | 4/2000 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | 0242459 A2 | 5/2005 |
| WO | 2005084190 A2 | 9/2005 |
| WO | 2005100392 A2 | 10/2005 |
| WO | WO 2007/014275 A2 | 1/2007 |
| WO | 2009009086 A2 | 1/2009 |

OTHER PUBLICATIONS

Mandell, et al., "Zinc Finger Tools: Custom DNA-Binding Domains for Transcription Factors and Nucleases," *Nucleic Acids Research* 34:W516-W523 (2006).
Mani, et al., "Design, Engineering and Characterization of Zinc Finger Nucleases," *Biochemical and Biophysical Research Communications* 335:447-457 (2005).
Miller, et al., "An Improved Zinc-Finger Nuclease Architecture for Highly Specific Genome Editing," 25(7):778-785 (2007).
Sander, et al., "Zinc Finger Targeter (ZiFiT): An Engineered Zinc Finger/Target Site Design Tool," *Nucleic Acids Research* 35:W599-W605 (2007).
Sander, et al., "Zinc Finger Targeter (ZiFiT): An Engineered Zinc Finger/Target Site Design Tool," *Nucleic Acids Research* 35:W599-W605 (May 25, 2007).
Segal, et al., "The Use of Zinc Finger Peptides to Study the Role of Sepcific Factor Binding Sites in the Chromatin Environment," *Methods* 26:76-83 (2002).
Santiago, et al., "Targeted Gene Knockout in Mammalian Cells by Using Engineered-Zinc Finger Nucleases," *PNAS* 105(15):5809-5814 (2008).
Uozumi, et al., "Purification and CDNA Cloning of Porcine Brain GDP-L-Fuc:n-Acetyl-Beta-D-Glucosaminide Alpha1->6fucosyltrasferase," *The Journal of Biological Chemistry* 271(44):27,810-27,817 (1998).
Yanagidani, et al., "Purification and CDNA Cloning of Porcine Brain GDP-L-Fuc:n-Acetyl-Beta-D-Glucosaminide Alpha1->6 Fucosyltrasferase (a1 -FucT) from Human Gastric Cancer MKN45 Cells," *J. Biochem.* 121(3):626-632 (1997).
Bae, et al., "One-Step Selection of Artificial Transcription Factors Using an In Vivo Screening System," *Molecules and Cells* 21:376-380 (2006).
Beerli, et al., "Engineering Polydactyl Zinc-Finger Transcription Factors," *Nature Biotechnology* 20:135-141 (2002).
Choo, et al., "Advances in Zinc Finger Engineering," *Curr. Opin. Struct. Biol.* 10:411-416 (2000).
Goodarzi et al., "Decreased Branching, Increased Fucosylation and Changed Sialylation of Alpha-1-Proteinase Inhibitor in Breast and Ovarian Cancer," *Clin Chim Acta* 236(2): 161-171 (1995).

Imai-Nishiya, et al, "Double Knockdown of A1,6-Fucosyltransferase (FUT8) and GDP-Mannose 4,6-Dehydratase (GMD) in Antibody-Producing Cells: A New Strategy for Generating Fully Non-Fucosylated Therapeutic Antibodies With Enhanced ADCC," *BMC Biotechnology* 7:84 (2007).
Isalan et al., "A Rapid, Generally Applicable Method to Engineer Zinc Fingers Illustrated by Targeting the HIV-1 Promoter," *Nat Biotechnol* 19:656-660 (2001).
Kanda, et al., "Establishment of a GDP-Mannose 4,6-Dehydratase (GMD) Knockout Host Cell Line: A New Strategy for Generating Completely Non-Fucosylated Recombinant Therapeutics," *J. Biotechnology* 130(3):300-310 (2007).
Kanda, et al., "Comparison of Biological Activity Among Nonfucosylated Therapeutic IGG1 Antibodies With Three Different N-Linked FC Oligosaccharides: The High-Mannose, Hybrid, and Complex Types," *Glycobiology* 17:104-118 (2006).
Kanda, et al., "Comparison of Cell Lines for Stable Production of Fucose-Negative Antibodies With Enhanced ADCC," *Biotechnology and Bioengineering* 94:680-688 (2006).
Kim, et al., "Chimeric Restriction Endonuclease," *PNAS USA* 91:883-887 (1994).
Kim, et al., "Insertion and Deletion Mutants of FOKI Restriction Endonuclease," *J. Biol. Chem.* 269:31978-31981 (1994).
Li, et al., "Functional Domains in FOK I Restriction Endonuclease," *PNAS USA* 89:4275-4279 (1992).
Li, et al., "Alteration of the Cleavage Distance of FOK I Restriction Endonuclease by Insertion Mutagenesis," *PNAS USA* 90:2764-2768 (1993).
Meng, et al., "Profiling the DNA-Binding Specificities of Engineered CYS2HIS2 Zinc Finger Domains Using a Rapid Cell-Based Method," *Nucleic Acids Res* 35:e81 (2007).
Mori, et al., "Engineering Chinese Hamster Ovary Cells to Maximize Effector Function of Produced Antibodies Using FUT8 Sirna," *Biotechnology Bioeng* 88:901-908 (2004).
Ohyama, et al., "Molecular Cloning and Expression of GDP-D-Mannose-4,6-Dehydratase, a Key Enzyme for Fucose Metabolism Defective in LEC13 Cells," *J Biol Chem* 273:14582-14587 (1998).
Oriol, et al, "Divergent Evolution of Fucosyltransferase Genes From Vertebrates, Invertebrates, and Bacteria," *Glycobiology* 9:323-334 (1999).
Pabo, et al., "Design and Selection of Novel CYS2-HIS2 Zinc Finger Proteins," *Ann. Rev. Biochem.* 70:313-340 (2001).
Ramirez, et al., "Unexpected Failure Rates for Modular Assembly of Enginnered Zinc Fingers," *Nature Methods* 5:374-375 (2008).
Ripka, et al., "Lectin-Resistant Cho Cells: Selection of Four New Pea Lectin-Resistant Phenotypes," *Somat Cell Mol Genet* 12:51-62 (1986).
Saitoh, et al., "Structural Analysis on the Sugar Chains of Human 1-Antitrypsin: Presence of Fucosylated Biantennary Glycan in Hepatocellular Carcinoma," *Archives Biochem & Biophysics* 303:281-287 (1993).
Satoh, et al., "Non-Fucosylated Therapeutic Antibodies as Next-Generation Therapeutic Antibodies," *Expert Opin Biol Ther* 6:1161-1173 (2006).
Segal, et al., "Custom DNA-Binding Proteins Come of Age: Polydactyl Zinc-Finger Proteins," *Curr. Opin. Biotechnol.* 12:632-637 (2001).
Shinkawa, et al., "The Absence of Fucose But Not the Presence of Galactose or Bisecting N-Acetylglucosamine of Human IGG1 Complex-Type Oligosaccharides Shows the Critical Role of Enhancing Antibody-Dependent Cellular Cytotoxicity," *JBC* 278:3466-3473 (2003).
Thompson, et al., "Fucosylated Forms of Alpha-1-Antitrypsin that Predict Unresponsiveness to Chemotherapy in Ovarian Cancer," *Br J Cancer* 58(5):589-593 (1988).
Urnov, et al., "Highly Efficient Endogenous Human Gene Correction Using Designed Zinc-Finger Nucleases," *Nature* 435:646-651 (2005).
Yamane-Ohnuki, et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," *Biotechnol Bioeng* 87:614-622 (2004).

(56) References Cited

OTHER PUBLICATIONS

Davis, et al., "Precision Genome Editing in Mammalian Cells Using Engineered Zinc Finger Protieins," SIGMA (2007).

Drier, et al., "Development of Zinc Finger Domains for Recognition of the 5'-Ann-3' Family of DNA Sequences and Their Use in the Construction of Artifical Transcription Factors," The Journal 276(31): 29466-29478 (2001).
U.S. Appl. No. 60/959,202, filed Jul. 12, 2007.
U.S. Appl. No. 60/993,624, filed Sep. 13, 2007.

FIG. 1: *C. griseus FUT8* cDNA sequence (SEQ ID NO:1)

aacagaaacttattttcctgtgtggctaactagaaccagagtacaatgtttccaattctttgagctccgagaagacagaaggagttgaaactctgaaaatgc
gggcgactggttcctggccgttggattatgctcattcttttgcctggggaccttattgtttatataggtggtcattggtcgagataatgaccaccctga
ccattctagcagagaactctccaagattcttgcaaagctggagctgagcgcttaaaacaacaaaatgaagacttgaggagaatgctgagtctctcgaataca
gaaggccctattgatcaggggcacagctcacaggaagagtccgtgttagaagaacagattgaaaattacaagaaacaa
gctaggaatgatctggaaggatcatgaaggaaatcttaaggaggagattgaaacatcttttggattaggacatcatgaaaggtctatcatgacagatctatactacctcagtc
aagaaattagaagaacgaactccaaagacatgcaaagtgcagataatcttttggatttaggacatcatgaaaggtctatcatgacagatctatactacctcagtc
aaacagatggagcaggtgagtggcgggaaaaagaagccaaagatgtgttggacatccaactccatcatgtggtttactgctcatgatgtttatggcacca
gcagcaaagccagaaaagctggtatgaattggcgctatccggaggatgggagactgtgttagacctgtaagtgagacatgcacagacaggtctggcc
tctccactgacactggtcaggtgaaagtgaagaacaaaatgttcaaagtggtcagataccttgagcagtgtcatcctgtctcctctactacctt
ggctgtaccagagaagacctgcagatcgactcgagagtccatgtgagaagcttgatcctgcagtggtgatcgcagtggatcctcaaataccttgatccgtccaacac
ttggctggaaagggaaatagaagaaccaccagaagaagcttggcttcaaacatccagttattggagtcagatcaggagcactgacaagtgggaacaga
agcagccttccatccattgaggaatacacgtacacgttgagaaacattcagcttctcgaacgcagaatgaatgttcggataaaaaagaagtgtatctgg
ccactgatgaccctttgttaaaggaggcaaagacaatgtactactccaattatgaatttattagtgatgataactctatttcttggtcagctgactacaaccgat
acacagaaaattcacttcggggcgtgatcctggatatacacttctctcccaggctgacttcctgtgttgtacttttcatccaggtctgtagggtgcttatga
aatcatgcaaactgcatcctgatgcctctgcaaacttccattcttagatgacatctacattttgaggccaaaatgcccaacaccagattgcagtttatcc
tcaccaactcgaactaaagaggaaaatccccatgaacctggagatatcattggttggctggaaaaccattgaatggttactctaaaggtgtcaacagaa
aactaggaaaaacaggctgtaccctttcctacaaagtcgagagaagatagaaacagtcaaatacctacatatcctgaagctgaaaaatagagaatgga
gtgtaagagattaacaacagaaatttagttcagacctccagccaagcagaagacc

FIG. 2: *C. griseus* Fut8 protein (SEQ ID NO:2)

mrawtgswrwimllfawgtllfyigghlvrdndhpdhssrelskilaklerlkqqnedlrmaeslripegpidqgtatgrvrvleeqlvkakeqienyk
kqarndlgkdheilrrriengakelwfflqselkklkkklegnelqrhadeilldlghhersimtdlyylsqtdgagewrekeakdltelvqrritylqnpkdc
skarklvcninkgcgygcqllhvvycfmiaygtqrtlilesqnwryatggwetvfrpvsetctdrsglstghwsgevkdknvqvvelpivdslhprpp
ylplavpedladrllrvhgdpavwwvsqfvkylirpqpwlereieettkklgfkhpvigvhvrrtdkvgteaafhpieeymvhveehfqllermkvd
kkrvylatddpsllkeaktkysnyeflsdnsiswsagllhmrytenslrgvildihflsqadflvctfssqvcrvayeimqtlhpdaasanfhslddiyyfggq
nahnqiavyphqprtkeeipmepgdiigvagnhwngyskgvnrklgktglypsykvrekietvkyptypeaek

FIG. 3: *C. griseus FUT8* genomic DNA (exon 9, intron 9, exon 10, intron 10 (partial)) (SEQ ID NO:3)

aggtgaagtgaaggagacaaaatgttcaagtggtcgagctcgagcagctccatcctcgtcctccttactacccttggctgtaccagaa
gacctgcagatcgactcctgagagtccatggtgatcctgcagtgtggtgggtatccagtttgtcaaatacttgatccgtccacaaccttggctgg
aagggaaatagaagaaccaccaagaagagcttggcttcaaacatccagttattgggtaagaatcatcccctcccttaaacagtaatatatagc
agtagttgtatgtgttttacttgtagatttttataatattaatagtcatagtcccaccaaagaacaaagattctaaaacttaaaagactattctccctt
tgttcagttagggcagcagagcaaatggtgcagtgtgtccttcgtcctctgatgctctcttcctttcattttttatgaagctcctggttttattttata
tttcctattccacaaattttcatctcttaatctttatatgtagagttgttactgaccccctcttcattgtatagaggtaacgaaagtacatagtgaaacca
gaatattaaatagtgttcatctcctcagacttcattgtggcacattctccctgcctcacttcattgtatagaacacacggaacaagtcc
aatttcctgagagaaacagtgattaagaggaatgtaggaaagaatgactgcatagttattcctgtggtcaaatccaactggactagtct
gggatgcaaaggaaacagtagcatgaaggtggcacagttaccccagtgctacagccctgactcagtgtctacagccctgatcaagacataacctgtctttggca
acactaagatgcaggagagtgctgggaagtgactggccattgcaggtcagtgtaagtctgtattcctgcttataacattgtgactttctca
aaatgagaaaatgaggtctgtttctgtttgcagttgatagagaaaaaaatgcaaaaaaagtctgtagtaacttaaattcatgaacataaataaccaaatc
tttaaaaggctagcttgttcttaaactacaggaaaagttcataagttacaagcattatctttttcagttacaagcttgaattctgttatgattttggtctcaaaaacca
gggtaaaatgaaagaaaaaaattaataaacttggcataagaatgttacaagttccaatattcttggatatgccaattactttcgtaagcaagtgtttcataaactttcatattg
aaaaacttaatctgttgattcagttccatataagtaattgtgaagtgttttgaaatgatttttatattttctaaggtgagaataatgtttaatatg
acctgtactattcaacattcagctatgttaagtactaggatactaattgagtacattatcagtgtgctctcccagagtccatgtcagacgcactgaca
tctccagtgccccatgactagggatactaattgagtaccagtacattatgttaaaggcaaagacaaagtagcgagcaaacaagttagaccaacaagtgcactgaca
aagtggaacagaagcagccttcatcccattgaggaatacacatgtgtacacgttgaagaacatttcagcttctcgaacgcagaagtggata
aaaaagagtgtatctgccactggccactgatgacccttcttgttaaaggaggcaaagacaaagtaagttagaccaacaagtggttctgtatggattatct
cttagttgaagaaaatcctaattctgggaacttgtggttcttgtgctaactaataggttccaaatcaaagactacatgcaaatattaatctaatca
agtcatacttactagctgtatctgatgcaaattaagaagtctaaaatgaattagaactgctgattttgtgcatcactagcagtcatcattcaacacag
taccacacttcttagtactaccaaatctgtttaacatactagagttccataaatcaaatttgtagcctgagcctgggggcttaagtaacagaagttatgtctcacag
ttctg FIG. 4
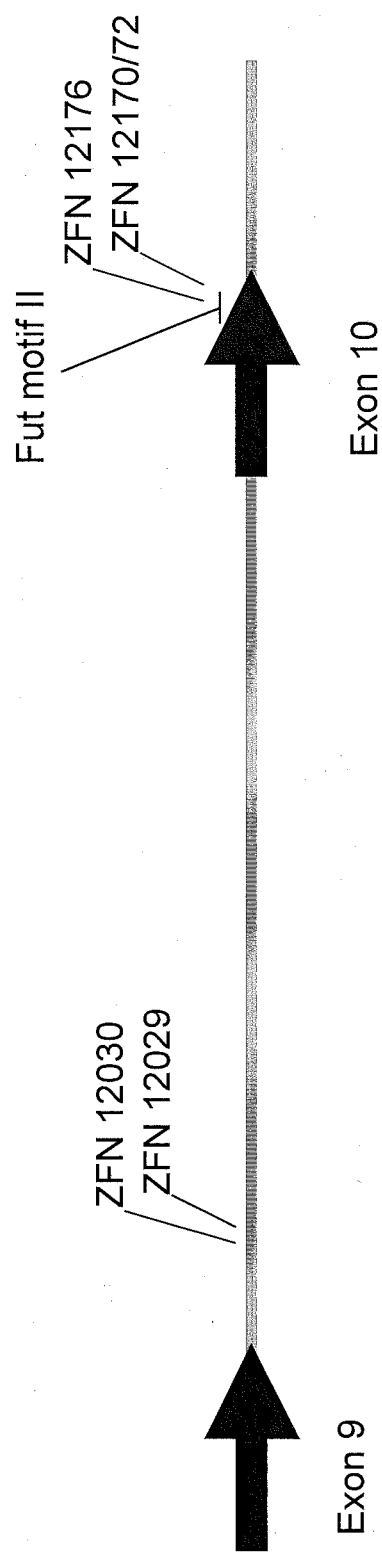
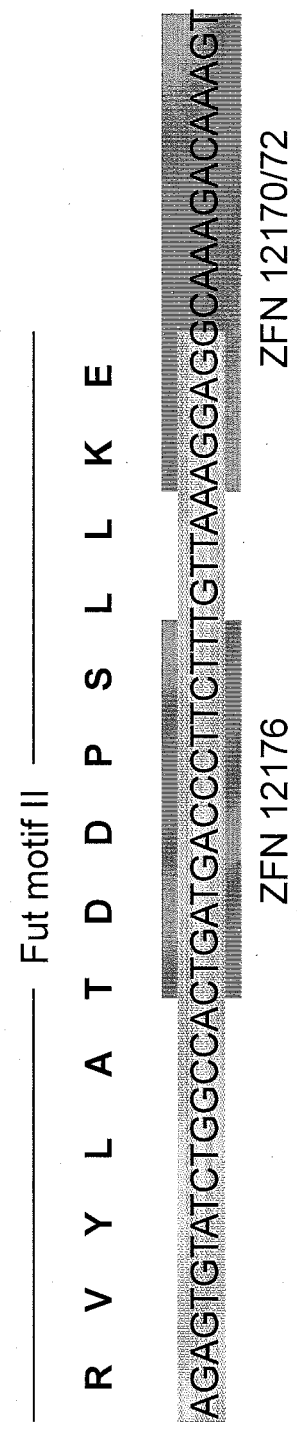

FIG 6
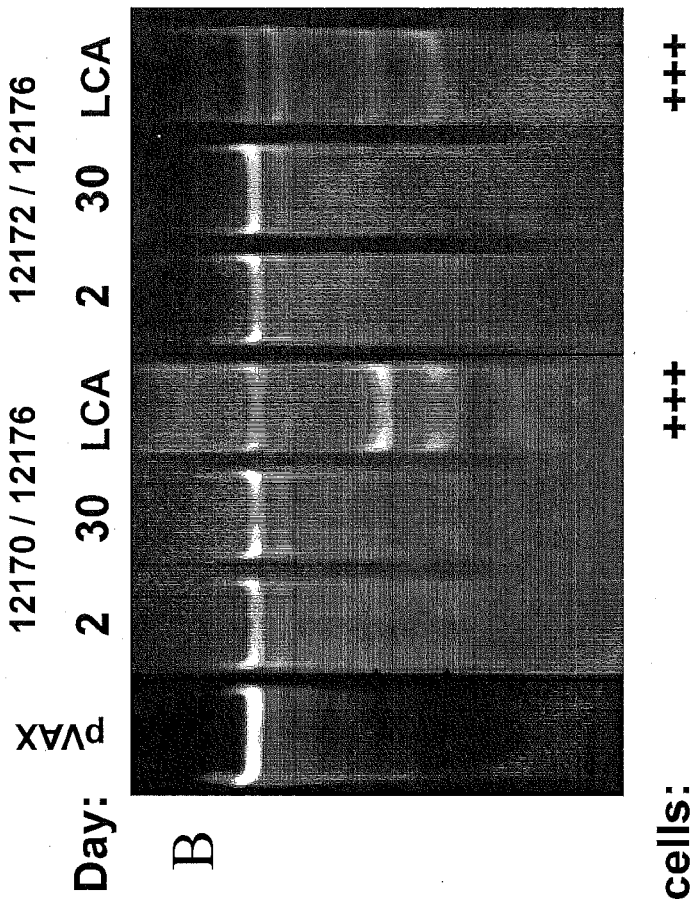
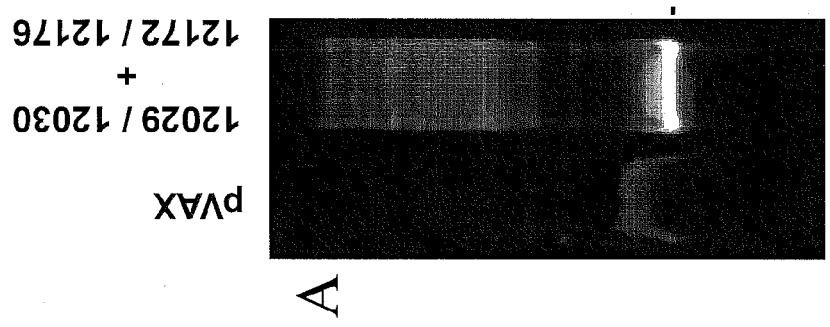

FIG. 8: Triple Knockout Clone Isolation from LCA-Enriched Pools

METHODS AND COMPOSITIONS FOR INACTIVATING ALPHA 1,6 FUCOSYLTRANSFERASE (FUT8) GENE EXPRESSION

CROSS-REFERENCE TO RELATED APPLICATIONS

The present application is a divisional application of U.S. patent application Ser. No. 12/931,265, filed Jan. 27, 2011, now allowed, which is a divisional application of U.S. patent application Ser. No. 12/218,035, filed Jul. 10, 2008, now U.S. Pat. No. 7,919,313, which claims the benefit of U.S. Provisional Application No. 60/959,202, filed Jul. 12, 2007 and U.S. Provisional Application No. 60/993,624, filed Sep. 13, 2007, the disclosures of which are hereby incorporated by reference in their entireties.

STATEMENT OF RIGHTS TO INVENTIONS MADE UNDER FEDERALLY SPONSORED RESEARCH

Not applicable.

TECHNICAL FIELD

The present disclosure is in the fields of genome engineering, cell culture and protein production.

BACKGROUND

Monoclonal antibody therapy is a large and growing treatment modality in medicine (Glennie et al. (2000) *Immunol Today* 21:403-10). There are more than twenty FDA-approved monoclonal antibody therapies, with many more currently in clinical trials. Antibody therapy directed against soluble factors (such as vascular endothelial growth factor or tumor necrosis factor, e.g.), aims simply to reduce the free ligand concentration by immunocomplex formation. In contrast, when antibody therapy is directed at cell surface antigens (as is often the case in anti-neoplastic immunotherapy), the goal is often the removal of the cell itself. The therapeutic antibody may induce apoptosis directly (Shan et al. (1998) *Blood* 91:1644-52; Shan (2000) *Cancer Immunol Immunother* 48:673-83), but more often it must recruit the patient's immune system to destroy the target cell. See, Reff et al. (1994) *Blood* 83:435-45; Idusogie et al. (2000) *J Immunol* 164:4178-84; Golay et al. (2000) *Blood* 95:3900-8; Harjunpaa et al. (2000) *Scand J Immunol* 51:634-41; Anderson et al. (1997) Biochem Soc Trans 25, 705-8; Clynes et al. (1998) *Proc Natl Acad Sci USA* 95:652-6; Clynes et al. (2000) *Nat Med* 6: 443-6; Sampson et al. (2000) *Proc Natl Acad Sci USA* 97:7503-8.

There are two main mechanisms by which the antibody-activated immune system can destroy offending cells: complement-dependent cytotoxicity (CDC) and antibody-dependent cellular cytotoxicity (ADCC). ADCC is an immune response generated primarily by natural killer (NK) cells against antibody-coated targets. See, Lewis et al. (1993) *Cancer Immunol Immunother* 37:255-63. In ADCC, NK cells recognize the constant (Fc) region of antibodies primarily via interaction with the NK cell's FcγRIII receptor. The NK cells then deposit perforins and granzymes on the target cell surface inducing cell lysis and apoptosis, respectively. The Fc-FcγRIII interaction is extremely sensitive to Fc glycosylation. Aglycosylated immunoglobulins fail to bind Fc receptors. See, Leatherbarrow et al. (1985) *Mol Immunol* 22:407-15 (1985); Walker et al. (1989) *Biochem J* 259:347-53 (1989); Leader et al. (1991) *Immunology* 72:481-5. In addition, fucosylation of the carbohydrate chain attached to Asn297 of the Fc region inhibits binding to FcγRIII and reduces in vitro ADCC activity. See, Shields et al. (2002) *J Biol Chem* 277: 26733-40; Shinkawa et al. (2003) J Biol Chem 278:3466-73; Niwa et al. (2004) *Cancer Res* 64:2127-33.

The majority of mammalian immunoglobulins are fucosylated, including those produced in Chinese hamster ovary cells (CHO cells, *Cricetulus griseus*). Jefferis et al. (1990) *Biochem J* 268:529-37; Hamako et al. (1993) *Comp Biochem Physiol B* 106:949-54; Raju et al. (2000) *Glycobiology* 10:477-86. Fucose attachment to the Fc core region is via an α-1,6 linkage generated by the α1,6 fucosyltransferase (Fut8) protein, apparently the sole α-1,6 fucosyltransferase in mammalian cells. Oriol et al. (1999) *Glycobiology* 9:323-34; Costache et al. (1997) *J Biol Chem* 272:29721-8. Disruption of the FUT8 gene in CHO cells eliminated core fucosylation of antibodies and increased ADCC by around 100-fold. See, Yamane-Ohnuki et al. (2004) *Biotechnol Bioeng* 87:614-22). However, such conventional gene disruption by homologous recombination is typically a laborious process. This was particularly true in the case of *C. griseus FUT*8, as approximately 120,000 clonal cell lines were screened to discover three healthy FUT8 −/− clones (Yamane-Ohnuki et al. (2004), supra).

Thus, there remains a need for cells lines in which Fut8 expression is partially or fully inactivated. Site-specific cleavage of genomic loci offers an efficient supplement and/or alternative to conventional homologous recombination. Creation of a double-strand break (DSB) increases the frequency of homologous recombination at the targeted locus more than 1000-fold. More simply, the inaccurate repair of a site-specific DSB by non-homologous end joining (NHEJ) can also result in gene disruption. Creation of two such DSBs can result in deletion of arbitrarily large regions. The modular DNA recognition preferences of zinc fingers protein allows for the rational design of site-specific multi-finger DNA binding proteins. Fusion of the nuclease domain from the Type II restriction enzyme Fok I to site-specific zinc finger proteins allows for the creation of site-specific nucleases. See, for example, United States Patent Publications 20030232410; 20050208489; 20050026157; 20050064474; 20060188987; 20060063231; and International Publication WO 07/014, 275, the disclosures of which are incorporated by reference in their entireties for all purposes.

SUMMARY

Disclosed herein are compositions for the partial or complete inactivation of a FUT8 gene. Also disclosed herein are methods of making and using these compositions (reagents), for example to inactivate FUT8 in a cell to produce cell lines in which a FUT8 gene is inactivated. FUT8 disrupted cell lines are useful, for example, in production of recombinant proteins such as α1-antitrypsin and monoclonal antibodies as antibodies produced in cells where Fut8 expression is reduced exhibit enhanced ADCC function.

In one aspect, zinc finger proteins, engineered to bind in a FUT8 gene, are provided. Any of the zinc finger proteins described herein may include 1, 2, 3, 4, 5, 6 or more zinc fingers, each zinc finger having a recognition helix that binds to a target subsite in a FUT8 gene. In certain embodiments, the zinc finger proteins comprise 4, 5 or 6 fingers (wherein the individual zinc fingers are designated F1, F2, F3, F4, F5 and F6) and comprise the amino acid sequence of the recognition helices shown in Table 1.

In certain embodiments, provided herein is an engineered zinc finger protein DNA-binding domain, wherein the DNA-binding domain comprises four zinc finger recognition regions ordered F1 to F4 from N-terminus to C-terminus, and wherein F1, F2, F3, and F4 comprise the following amino acid sequences: F1: QSSDLSR (SEQ ID NO:9); F2: TSGNLTR (SEQ ID NO:10); F3: RSDDLSK (SEQ ID NO:11); and F4: DRSALAR (SEQ ID NO:12).

In other embodiments, the disclosure provides an engineered zinc finger protein DNA-binding domain, wherein the DNA-binding domain comprises four zinc finger recognition regions ordered F1 to F4 from N-terminus to C-terminus, and wherein F1, F2, F3, and F4 comprise the following amino acid sequences: F1: RSDVLSA (SEQ ID NO:14); F2: QNATRIN (SEQ ID NO:15); F3: DRSNLSR (SEQ ID NO:16); and F4: RLDNRTA (SEQ ID NO:17).

In other embodiments, the disclosure provides an engineered zinc finger protein DNA-binding domain, wherein the DNA-binding domain comprises six zinc finger recognition regions ordered F1 to F6 from N-terminus to C-terminus, and wherein F1, F2, F4, F5 and F6 comprise the following amino acid sequences: F1: RSDNLSV (SEQ ID NO:19); F2: QNATRIN (SEQ ID NO:15); F4: QSATRTK (SEQ ID NO:21); F5 RSDNLSR (SEQ ID NO:22); and F6: RNDNRKT (SEQ ID NO:23). In any of these embodiments, F3 may comprise RSDNLST (SEQ ID NO:20) or RSDHLSQ (SEQ ID NO:24).

In other embodiments, the disclosure provides an engineered zinc finger protein DNA-binding domain, wherein the DNA-binding domain comprises five zinc finger recognition regions ordered F1 to F5 from N-terminus to C-terminus, and wherein F1, F2, F3, F4, and F5 comprise the following amino acid sequences: F1: RSDNLRE (SEQ ID NO:26); F2: NNTQLIE (SEQ ID NO:27); F3: TSSILSR (SEQ ID NO:28); F4 RSDNLSA (SEQ ID NO:29); and F5: RKDTRIT (SEQ ID NO:30).

In another aspect, fusion proteins comprising any of the zinc finger proteins described herein and at least one cleavage domain or at least one cleavage half-domain, are also provided. In certain embodiments, the cleavage half-domain is a wild-type FokI cleavage half-domain. In other embodiments, the cleavage half-domain is an engineered FokI cleavage half-domain.

In yet another aspect, a polynucleotide encoding any of the proteins described herein is provided.

In yet another aspect, also provided is an isolated cell comprising any of the proteins and/or polynucleotides as described herein. In certain embodiments, Fut8 is inactivated (partially or fully) in the cell. Any of the cells described herein may include additional genes that have been inactivated, for example, using zinc finger nucleases designed to bind to a target site in the selected gene. In certain embodiments, provided herein are cells or cell lines in which FUT8, dihydrofolate reductase (DHFR) and glutamine synthetase (GS) have been inactivated.

In addition, methods of using the zinc finger proteins and fusions thereof in methods of inactivating FUT8 in a cell or cell line are provided. In certain embodiments, inactivating a FUT8 gene results in a cell line which can produce recombinant proteins at higher levels or in which one or more activities (functions) of the proteins are increased as compared to proteins produced in cells where the FUT8 gene is not inactivated. For example, cell lines as described herein having an inactivated FUT8 gene can be used to produce monoclonal antibodies that exhibit enhanced ADCC function for immunotherapy. Cell lines as described herein can also be used to produce recombinant α1-antitrypsin.

Thus, in another aspect, provided herein is a method for inactivating a cellular FUT8 gene (e.g., an endogenous FUT8 gene) in a cell, the method comprising: (a) introducing, into a cell, a first nucleic acid encoding a first polypeptide, wherein the first polypeptide comprises: (i) a zinc finger DNA-binding domain that is engineered to bind to a first target site in an endogenous FUT8 gene; and (ii) a cleavage domain; such that the polypeptide is expressed in the cell, whereby the polypeptide binds to the target site and cleaves the FUT8 gene. In certain embodiments, the methods further comprise introducing a nucleic acid encoding a second polypeptide, wherein the second polypeptide comprises: (i) a zinc finger DNA-binding domain that is engineered to bind to a second target site in the FUT8 gene; and (ii) a cleavage domain; such that the second polypeptide is expressed in the cell, whereby the first and second polypeptides bind to their respective target sites and cleave the FUT8 gene. The first and second polypeptides may be encoded by the first nucleic acid or by different nucleic acids. In certain embodiments, one or more additional polynucleotides or polypeptides are introduced into the cells, for example polynucleotides encoding additional zinc finger proteins.

In yet another aspect, the disclosure provides a method of producing a recombinant protein of interest in a host cell, the method comprising the steps of: (a) providing a host cell comprising an endogenous FUT8 gene; (b) inactivating the endogenous FUT8 gene of the host cell by any of the methods described herein; and (c) introducing an expression vector comprising a transgene, the transgene comprising a sequence encoding a protein of interest, into the host cell, thereby producing the recombinant protein. In certain embodiments, the protein of interest comprises an antibody, e.g., a monoclonal antibody.

In any of the cells and methods described herein, the cell or cell line can be a COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cell such as *Spodoptera fugiperda* (Sf), or fungal cell such as *Saccharomyces, Pichia* and *Schizosaccharomyces*.

BRIEF DESCRIPTION OF THE DRAWINGS

FIG. 1 depicts the nucleotide sequence of *C. griseus* FUT8 cDNA sequence (SEQ ID NO:1).

FIG. 2 depicts the amino acid sequence of *C. griseus* Fut8 (SEQ ID NO:2).

FIG. 3 depicts partial nucleotide sequence of exon 9, intron 9, exon 10 and intron 10 of *C. griseus* FUT8 genomic DNA (SEQ ID NO:3).

FIG. 4, panels A and B, are schematics depicting the location of zinc finger nuclease (ZFN) binding and cleavage sites within FUT8 exon 10. FIG. 4A is an overview of the exon 9-intron 10 region. Exons are depicted with black arrows and the grey line shows non-coding DNA. FIG. 4B shows a detailed view of the fucosyltransferase motif II and ZFN binding sites. The location of the fucosyltransferase motif II (light grey box) was determined as described in Oriol et al. (1999) *Glycobiology* 9:323-34 (1999). The translation of the Fut motif II is shown above the DNA sequence (SEQ ID NOS: 65 and 66, respectively). The location of the recognition sequences of the ZFNs in relation to the sense strand of the gene are shown as dark grey boxes. ZFN 12176 (Table 1) is a five Zn-finger protein recognizing a 15 bp target site and ZFN 12170 (Table 1) is a six Zn-finger protein recognizing 18 bp target site. The last two nucleotides shown (GT) are the 5' splice donor site for intron 10.

FIG. 5A shows Cel-1 assays results for DNA harvested two days post-transfection of the indicated plasmids and a portion of the FUT8 locus PCR amplified using the oligos GJC 71F: GCT-TGGCTTCAAACATCCAG (SEQ ID NO:4) and GJC 89R: GGACTTGTTCCGTGTGTTCT (SEQ ID NO:5). The sizes of the predicted cleavage products are 264 bp and 216 bp. FIG. 5B shows results of DNA was harvested two days post-transfection and a portion of the FUT8 locus PCR amplified using the oligos GJC 90F: CTGTTGATTCCAGGTTCCCA (SEQ ID NO:6) and GJC 91R: TGTTACTTAAGC-CCCAGGC (SEQ ID NO:7). The sizes of the predicted cleavage products are 431 bp and 342 bp. ZFN combinations are shown above the appropriate lanes; ZFN-specific cleavage products are indicated with white arrowheads. The percent of chromosomes modified by non-homologous end joining is listed below each lane. The size of molecular weight marker bands is indicated to the left of the gel.

FIG. 6, panels A and B, depict ZFN activity at the endogenous FUT8 locus. FIG. 6A shows results of nuclease-mediated deletion of 1.3 kb of FUT8 using the two indicated ZFN pairs, which were transfected in parallel, with the genomic DNA harvested two days later. Deletion of the ~1300 bp between the ZFN sites generates a ~559 bp product. FIG. 6B results of Cel-1 mismatch assays for ZFN activity at the endogenous FUT8 locus with and without $Lens\ culinaris$ agglutinin (LCA) enrichment in CHO cells. ZFN pairs are shown at the top line (ZFN pair 12170 and 12176 for lanes 2 to 4 (from left to right) and ZFN pair 12172 and 12176 for lanes 5 to 7 (from left to right)). The lane designated "pVAX" refers to control cells transfected with empty plasmid (no ZFN). The lane designations "2" and "30" refer to days post-transfection and "LCA" refers to cells subject to LCA selection.

DETAILED DESCRIPTION

Figure 5:
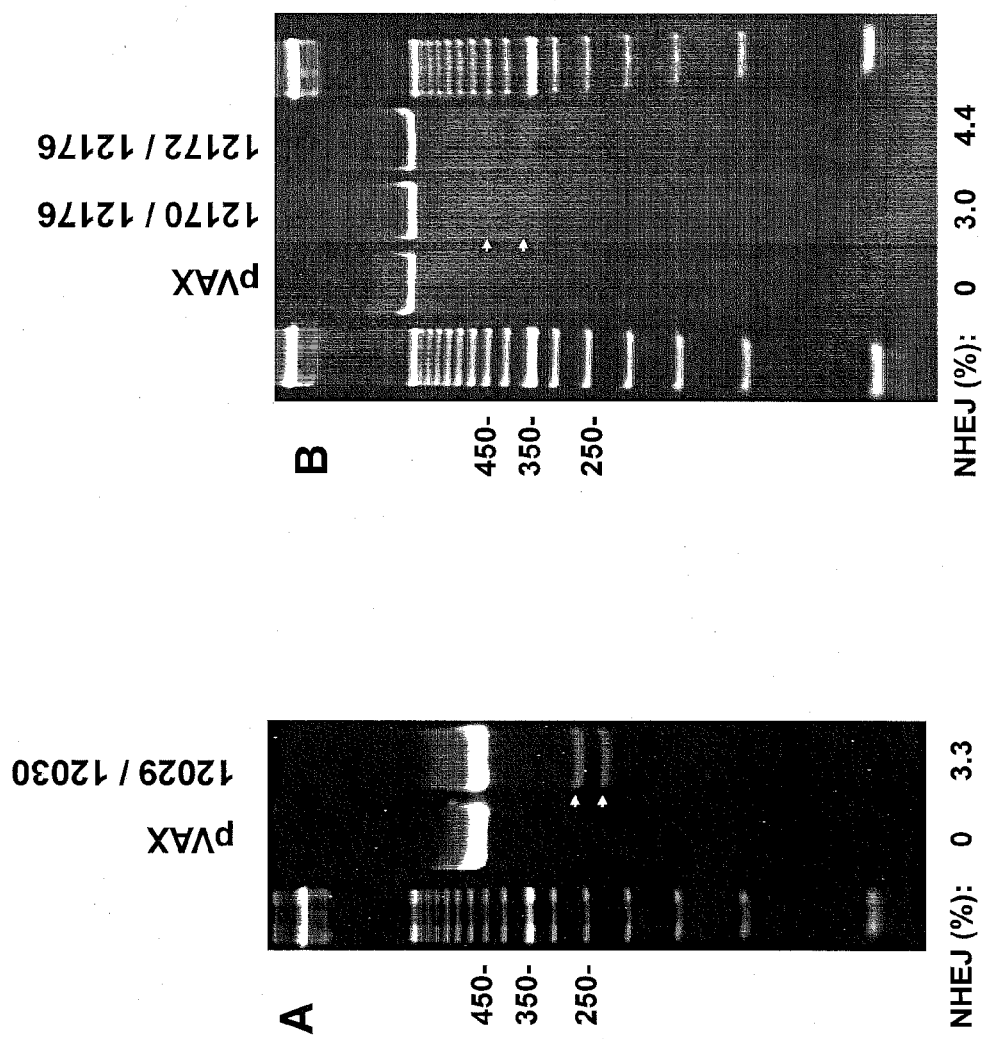
FIG. 5, panels A and B, show results of Cel-1 mismatch assays for ZFN activity at the endogenous FUT8 locus. The efficacy of each ZFN pair is reflected in the total amount of cleavage products beneath the parent PCR product.

Described herein are compositions and methods for partial or complete inactivation of a FUT8 gene. Also disclosed are methods of making and using these compositions (reagents), for example to inactivate a Fut8 gene in a target cell. Inactivation of Fut8 in a target cell can be used to produce cell lines for expression of recombinant proteins, particularly monoclonal antibodies that elicit enhanced ADCC.

In mammalian cells, Fut8 attaches core fucose to the oligosaccharides present on the Fc region of antibodies, which is widely recognized as being of great importance for the effector function of antibody-dependent cellular cytotoxicity. Three-dimensional analysis of the structure of human Fut8 has shown that the three α2/α6 fucosyltransferase motifs form the catalytic core of the enzyme. See, Ihara et al. (2007) $Glycobiology$ 17:455-66. In this region, point mutation of many single residues to alanine results in complete inactivation of the enzyme. See, Ihara et al. (2007) $Glycobiology$ 17:455-66; Takahashi et al. (2000) $Glycobiology$ 10:503-10. As noted above, cells in which FUT8 expression is reduced or eliminated (e.g. knockout cell lines or with siRNA), produce non-fucosylated antibodies that have greater effector function. See, e.g., Kanada et al. (2007) $Biotechnol.$ 130(3):300-310; Kanada et al. (2007) $Glycobiology$ 18:104-118; Mori et al. (2004) $Biotechnol.\ Bioeng.$ 88:901-908.

Thus, the methods and compositions described herein provide a highly efficient method for targeted gene knockout (partial or complete) of FUT8 that allows for the generation of cells lines for producing non-fucosylated proteins such as antibodies.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolfe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

An "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain) See, also, U.S. Patent Publication Nos. 2005/0064474; 2007/0218528 and 2008/0131962, incorporated herein by reference in their entireties.

"Chromatin" is the nucleoprotein structure comprising the cellular genome. Cellular chromatin comprises nucleic acid, primarily DNA, and protein, including histones and nonhistone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases. An exogenous molecule can also be the same type of molecule as an endogenous molecule but derived from a different species than the cell is derived from. For example, a human nucleic acid sequenced may be introduced into a cell line originally derived from a mouse or hamster.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, shRNAs, micro RNAs (miRNAs) ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Gene inactivation refers to any reduction in gene expression as compared to a cell that does not include a ZFP as described herein. Thus, gene inactivation may be complete (knock-out) or partial (e.g., a hypomorph in which a gene exhibits less than normal expression levels or a product of a mutant gene that shows partial reduction in the activity it influences).

"Eucaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

The term "antibody" as used herein includes antibodies obtained from both polyclonal and monoclonal preparations, as well as, the following: hybrid (chimeric) antibody molecules (see, for example, Winter et al., Nature (1991) 349: 293-299; and U.S. Pat. No. 4,816,567); F(ab')2 and F(ab) fragments; Fv molecules (non-covalent heterodimers, see, for example, Inbar et al., Proc Natl Acad Sci USA (1972) 69:2659-2662; and Ehrlich et al., Biochem (1980) 19:4091-4096); single-chain Fv molecules (sFv) (see, for example, Huston et al., Proc Natl Acad Sci USA (1988) 85:5879-5883); dimeric and trimeric antibody fragment constructs; minibodies (see, e.g., Pack et al., Biochem (1992) 31:1579-1584; Cumber et al., J Immunology (1992) 149B: 120-126); humanized antibody molecules (see, for example, Riechmann et al., Nature (1988) 332:323-327; Verhoeyan et al., Science (1988) 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the teen "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

Zinc Finger Nucleases

Described herein are zinc finger nucleases (ZFNs) that can be used for inactivation of a FUT8 gene. ZFNs comprise a zinc finger protein (ZFP) and a nuclease (cleavage) domain.

A. Zinc Finger Proteins

Zinc finger binding domains can be engineered to bind to a sequence of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789, 538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length (e.g., TGEKP (SEQ ID NO:36), TGGQRP (SEQ ID NO:37), TGQKP (SEQ ID NO:38), and/or TGSQKP (SEQ ID NO:39)). See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. Examples of additional linker structures are found in U.S. Provisional Application No. 61/130,099, filed May 28, 2008 and entitled Compositions For Linking DNA-Binding Domains And Cleavage Domains.

Table 1 describes a number of zinc finger binding domains that have been engineered to bind to nucleotide sequences in the FUT8 gene. See, also, FIG. 1 and FIG. 3. Each row describes a separate zinc finger DNA-binding domain. The DNA target sequence for each domain is shown in the first column and the second through fifth columns show the amino acid sequence of the recognition region (amino acids −1 through +6, with respect to the start of the helix) of each of the zinc fingers (F1 through F4, F5 or F6) in the protein. Also provided in the first column is an identification number for the proteins.

One or more pairs of such zinc finger/nuclease half-domain fusions are used for targeted cleavage, as disclosed, for example, in U.S. Patent Publication Nos. 20050064474 and 20070218528.

For targeted cleavage, the near edges of the binding sites can separated by 5 or more nucleotide pairs, and each of the fusion proteins can bind to an opposite strand of the DNA target. All pairwise combinations (e.g., ZFN 12029 with ZFN 12030, and ZFN 12170 with either ZFN 12172 or ZFN 12176) of the proteins shown in Table 1 can be used for targeted cleavage of a FUT8 gene. Following the present disclosure, ZFNs can be targeted to any sequence in a FUT8 gene.

B. Cleavage Domains

The ZFNs also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two

TABLE 1

Zinc finger nucleases targeted to Fut8

| ZFN name Target sequence | F1 | F2 | F3 | F4 | F5 | F6 |
|---|---|---|---|---|---|---|
| ZFN 12029 GTCTCGGATGCT (SEQ ID NO: 8) | QSSDLSR (SEQ ID NO: 9) | TSGNLTR (SEQ ID NO: 10) | RSDDLSK (SEQ ID NO: 11) | DRSALAR (SEQ ID NO: 12) | N/A | N/A |
| ZFN 12030 AAGGACACACTG (SEQ ID NO: 13) | RSDVLSA (SEQ ID NO: 14) | QNATRIN (SEQ ID NO: 15) | DRSNLSR (SEQ ID NO: 16) | RLDNRTA (SEQ ID NO: 17) | N/A | N/A |
| ZFN 12170 AAGGAGGCAAAG ACAAAG (SEQ ID NO: 18) | RSDNLSV (SEQ ID NO: 19) | QNATRIN (SEQ ID NO: 15) | RSDNLST (SEQ ID NO: 20) | QSATRTK (SEQ ID NO: 21) | RSDNLSR (SEQ ID NO: 22) | RNDNRKT (SEQ ID NO: 23) |
| ZFN 12172 AAGGAGGCAAAG ACAAAG (SEQ ID NO: 18) | RSDNLSV (SEQ ID NO: 19) | QNATRIN (SEQ ID NO: 15) | RSDHLSQ (SEQ ID NO: 24) | QSATRTK (SEQ ID NO: 21) | RSDNLSR (SEQ ID NO: 22) | RNDNRKT (SEQ ID NO: 23) |
| ZFN 12176 AAGAAGGGTCATCAG (SEQ ID NO: 25) | RSDNLRE (SEQ ID NO: 26) | NNTQLIE (SEQ ID NO: 27) | TSSILSR (SEQ ID NO: 28) | RSDNLSA (SEQ ID NO: 29) | RKDTRIT (SEQ ID NO: 30) | N/A |

As described below, in certain embodiments, a four-, five-, or six-finger binding domain as shown in Table 1 is fused to a cleavage half-domain, such as, for example, the cleavage domain of a Type IIs restriction endonuclease such as FokI.

cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished when one or more pairs of nucleases containing these cleavage half-domains are used for cleavage. See, e.g., U.S. Patent Publication No. 20080131962, the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in U.S. Patent Publication Nos. 20050064474 (Example 5) and 20070134796 (Example 38).

C. Additional Methods for Targeted Cleavage in FUT8

Any nuclease having a target site in a FUT8 gene can be used in the methods disclosed herein. For example, homing endonucleases and meganucleases have very long recognition sequences, some of which are likely to be present, on a statistical basis, once in a human-sized genome. Any such nuclease having a unique target site in a FUT8 gene can be used instead of, or in addition to, a zinc finger nuclease, for targeted cleavage in a FUT8 gene.

Exemplary homing endonucleases include I-SceI, I-CeuI, PI-PspI, PI-Sce, I-SceIV, I-CsmI, I-PanI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66.

Delivery

The ZFNs described herein may be delivered to a target cell by any suitable means. Suitable cells include but not limited to eukaryotic and prokaryotic cells and/or cell lines. Non-limiting examples of such cells or cell lines include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*.

Methods of delivering proteins comprising zinc fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

FUT8 ZFNs as described herein may also be delivered using vectors containing sequences encoding one or more of the ZFNs. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more ZFN encoding sequences. Thus, when one or more pairs of ZFNs are introduced into the cell, the ZFNs may be carried on the same vector or on different vectors. When multiple vectors are used, each vector may comprise a sequence encoding one or multiple ZFNs.

Conventional viral and non-viral based gene transfer methods can be used to introduce nucleic acids encoding engineered ZFPs in cells (e.g., mammalian cells) and target tissues. Such methods can also be used to administer nucleic acids encoding ZFPs to cells in vitro. In certain embodiments, nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids encoding engineered ZFPs include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.) and Copernicus Therapeutics Inc., (see for example U.S. Pat. No. 6,008,336).

Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Vivol.* 63:2374-2378 (1989); Miller et al., *J. Virol.* 65:2220-2224 (1991); PCT/US94/05700).

In applications in which transient expression of a ZFP fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (see Inaba et al., *J. Exp. Med.* 176:1693-1702 (1992)).

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pichia* and *Schizosaccharomyces*. Progeny, variants and derivatives of these cell lines can also be used.

Applications

The disclosed methods and compositions can be used for inactivation of a FUT8 genomic sequence. As noted above, inactivation includes partial or complete repression of FUT8 gene expression in a cell. Inactivation of a FUT8 gene can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript.

There are a variety of applications for ZFN-mediated inactivation (knockout or knockdown) of FUT8. For example, the methods and compositions described herein allow for the generation of Fut8-deficient cell lines for use in recombinant protein production, for example α1-antitrypsin and/or monoclonal antibody production. Cells in which Fut8 is inactivated produce antibodies that exhibit greater effector function, particularly in the induction of ADCC.

Similarly, cells in which Fut8 is partially or completely inactivated can also be used to produce the fucosylated serine protease inhibitor alpha 1-Antitrypsin or α1-antitrypsin (A1AT). A1AT may play a role in the inhibition of cancer metastasis (Goodarzi and Turner (1995) Chim Acto 236(2): 161-171) and patients afflicted with a variety of cancers exhibit A1AT which is more heavily fucosylated as compared to that found in the normal population (Saitoh et al. (1993) *Archives Biochem. & Biophysics* 303:281-287), suggesting that fucosylation of the endogenous A1AT may lead to decreased functionality. In addition, it has been shown that the presence of fucosylated A1AT in ovarian cancer patients is predictive of unresponsiveness to chemotherapy (Thompson et al. (1988) *Br. J. Cancer* 58(5):89-93). Alpha 1-antitrypsin isolated from blood plasma has been used for the treatment of lung degradation (e.g., pulmonary emphysema) caused by a lack of A1AT. Production of A1AT in a fut8 knockout or knockdown cell line could yield protein with greater consistency and activity. Thus, the cells and cell lines described herein also allow for the efficient production of A1AT.

Additional genes in the Fut8 deficient cells and cells lines described herein may also be inactivated. Additional genes involved in protein overexpression as well as compositions and methods for inactivating these genes are disclosed in U.S. Patent Publication Nos. 2006/0063231 and 20080015164, the disclosures of which are incorporated by reference in their entireties herein. For instance, as disclosed in Example 5, cells can be generated using the methods described herein in which Fut8, dihydrofolate reductase (DHFR) and glutamine synthetase (GS) have been inactivated. See, Example 5. These cells are useful for overexpressing a protein of interest.

EXAMPLES

Example 1

Design and Construction of FUT8 ZFNs

Three motifs conserved across α-2 and α-6 fucosyltransferases are responsible for enzymatic activity of Fut8 and subsequent fucosylation of recombinantly produced antibody therapeutics. See, Ihara et al. (2007) *Glycobiology* 17:455-66. These motifs were readily identifiable in the hamster (*C. griseus*) sequence. See, Oriol et al. (1999) *Glycobiology* 9:323-34; Javaud et al. (2000) *Mol Biol Evol* 17:1661-72. In particular, the hamster FUT8 Fut motif II (FIG. 4) is identical to the cow and human motifs, and only one amino acid different than those from pig and mouse. Javaud et al. (2000) *Mol Biol Evol* 17:1661-72. In addition, alignment of *M. musculus* and *R. norvegicus* FUT8 genomic DNA sequence suggested that intron 9 of the *C. griseus* FUT8 gene would be small enough to be readily clonable.

The *C. griseus* FUT8 cDNA was cloned as follows. Ten nanograms of a cDNA library derived from CHO-S cells was PCR amplified using primers GJC 119F: AACAGAAACT-TATTTTCCTGTGT (SEQ ID NO:31) and GJC 106R: GGTCTTCTGCTTGGCTGAGA (SEQ ID NO:32), cloned using TOPO™ (Invitrogen) and sequenced. Similarly, FUT8 intron 9 was PCR amplified from *C. griseus* genomic DNA using EasyA™ polymerase (Stratagene) and the oligonucleotide primers GJC 71F: GCTTGGCTTCAAACATCCAG (SEQ ID. NO:4) and GJC 72R: CACTTTGTCAGT-GCGTCTGA (SEQ ID NO:33). The PCR product was cloned and sequenced. The partial sequence of intron 10 was obtained by PCR amplification of *C. griseus* genomic DNA using EasyA™ polymerase (Stratagene) and the oligonucleotides GJC 75F: AGTCCATGTCAGACGCACTG (SEQ ID NO:34) and GJC 77R: CAGAACTGTGAGACATAAACTG (SEQ ID NO:35).

The FUT8 cDNA, intron 9 and intron 10 sequences cloned as described above were then used for the design of ZFNs binding within FUT8. In particular, the FUT8 cDNA (FIG. 1) sequence was scanned for sites favorable for recognition by zinc finger nucleases, and one such location that overlapped with the Fut8 enzymatic motif was identified (FIG. 4). In addition, the intronic DNA (FIG. 3) was also scanned for potential ZFN binding sites.

Several pairs of zinc finger nucleases (ZFNs) were designed to recognize sequences within FUT8. The approximate locations of two ZFN sites in the FUT8 gene are shown in FIG. 4. The sequences of the zinc finger recognition helices and the DNA sequences they are designed to recognize are listed in Table 1. Plasmids comprising sequences encoding FUT8 ZFNs were constructed essentially as described in Urnov et al. (2005) *Nature* 435(7042):646-651.

Example 2

Cel-1 Mismatch Assay

To determine whether FUT8-targeted ZFNs modified the endogenous FUT8 locus as expected, Cel-1 mismatch assays were performed essentially as per the manufacturer's instructions (Trangenomic SURVEYOR™). Briefly, the appropriate ZFN plasmid pairs were transfected into CHO K-I cells. CHO K-I cells were obtained from the American Type Culture Collection and grown as recommended in F-12 medium (Invitrogen) supplemented with 10% qualified fetal calf serum (FCS, Hyclone). Cells were disassociated from plasticware using TrypLE Select™ protease (Invitrogen). For transfection, one million CHO K-I cells were mixed with 1 µg each zinc finger nuclease and 100 µL Amaxa Solution T. Cells were transfected in an Amaxa Nucleofector II™ using program U-23 and recovered into 1.4 mL warm F-12 medium+10% FCS.

Cells were harvested two days post-transfection and chromosomal DNA prepared using a Masterpure™ DNA Purification Kit (Epicentre). The appropriate region of the FUT8 locus was PCR amplified using Accuprime™ High-fidelity DNA polymerase (Invitrogen). PCR reactions were heated to 94° C., and gradually cooled to room temperature. Approximately 200 ng of the annealed DNA was mixed with 0.334 CEL-I™ enzyme (Transgenomic) and incubated for 20 minutes at 42° C. Reaction products were analyzed by polyacrylamide gel electrophoresis in 1× Tris-borate-EDTA buffer.

As shown in FIGS. 5A and 5B, FUT8 ZFNs modified the endogenous FUT8 locus. In particular, ZFN pair of ZFN 12029 and ZFN 12030 resulted in modification of 3.3% of chromosomes (FIG. 5A). ZFN pairs 12170/12176 and 12172/12176 modified 3.0% and 4.4% of chromosomes, respectively (FIG. 5B).

Example 3

Genotypic Analysis

FUT8 deletion clones were also analyzed at the genetic level. In order to rapidly identify double-mutant clones, a phenotypic screen based on the resistance of fucosylation-deficient CHO cells to the lectin *Lens culinaris* agglutinin (LCA, Vector Laboratories) was used. The CHO cell line Lec13 contains a mutation in the fucose biosynthetic gene GMD that allows it to grow in concentrations of LCA 50-fold higher than wild-type CHO cells. See, e.g., Ripka et al. (1986) *Somat Cell Mol Genet* 12: 51-62; Ohyama et al. (1998) *J Biol Chem* 273:14582-7. FUT8−/− cells fail to bind fluorescently-labeled LCA. See, Yamane-Ohnuki et al. (2004) *Biotechnol Bioeng* 87:614-22. Accordingly, we reasoned that FUT8−/− cells would also be resistant to growth in LCA.

Cells were transfected as described in Example 2 using the ZFN pair 12170/12176, except that between 6 and 30 days post-transfection, the ZFN-treated cells were plated into 96-well format at limiting dilution, at approximately 0.4 cells/well. After two weeks of growth the number of clones per well was scored, the cells washed in 1×PBS, and 20 µL TrypLE Select™ (InVitrogen) added. Ten microliters of the disassociated cells were transferred to parallel 96-well plates containing F-12 medium+10% FCS+50 µg/mL LCA. One-hundred microliters of F-12 medium+10% FCS was added to the remaining 10 µL of cells in the original 96-well plate. The morphology of cells in the LCA-containing plates was scored 18 hours later. Clones retaining a wild-type non-rounded CHO-KI morphology in the presence of LCA were noted and the corresponding colony from the non-LCA-treated plate was expanded. If the original well was found to contain more than one clone (and also therefore produce a mixture of rounded and wild-type-appearing cells when grown in LCA), the contents of the well were redilution cloned as above.

Genomic DNA was harvested from non-LCA-treated LCA-resistant cells and a portion of the FUT8 locus PCR amplified using the oligos GJC 75F:

```
                                    (SEQ ID NO: 34)
AGTCCATGTCAGACGCACTG
and GJC 91R:

(SEQ ID NO: 7)
TGTTACTTAAGCCCCAGGC.
```

Half of the PCR product (~200 ng) was analyzed using the CEL-I assay as described above while the other half was gel purified. Purified bands that were CEL-I-negative (homozygotes) were sequenced directly. CEL-I-positive bands were Topo®-Cloned (Invitrogen) and clones sequenced until two alleles were recovered.

Of the 600 clones analyzed in this manner, 28 were resistant to LCA (4.7%). Fifteen of the 28 LCA-resistant cell lines were single-cell clones. Cell lines were expanded from the half of the culture not exposed to LCA. The FUT8 genotypes of these clones are shown in Table 2. The region of sequence shown here is identical to that shown in FIG. 4. A five base pair gap has been inserted into this depiction of the wild-type sequence to accommodate allelic sequences that contain the small insertions found in some clones. Alleles are designated as A and B; clones without allele designations are homozygous. Clone 12-B contains a 148 bp insertion of *C. griseus* ribosomal DNA (rDNA) sequence as well as the indicated deletion.

TABLE 2

| LCA-resistant clones treated with the ZFN pair 12170/12176 |
|---|
| Clone Partial Sequence |
| Wild type AGAGTGTATCTGGCCACTGATGACCCTTCTTT-----GTTAAAGGAGGCAAAGACAAAGTAAGT (SEQ ID NO: 40) |

TABLE 2-continued

LCA-resistant clones treated with the ZFN pair 12170/12176

Clone   Partial Sequence

1-A   AGAGTGTATCTGGCCACTGATGACCCTT-----------TAAGGAGGCAAAGACAAAGTAAGT
      (SEQ ID NO: 41)

1-B   AGAGTGTATCTGGCCACTGATGACCCTTCTTTGTTA---TAAAGGAGGCAAAGACAAAGTAAGT
      (SEQ ID NO: 42)

2-A   AGAGTGTATCTGGCCACTG-----------------------------AAAGACAAAGTAAGT
      (SEQ ID NO: 43)

2-B   AGAGTGTATCTGGCCACTGATGACC------------GTTAAAGGAGGCAAAGACAAAGTAAGT
      (SEQ ID NO: 44)

3-A   AGAGTGTATCTGGCCACTGATGACCCTTCTTTGTTATGTTAAAGGAGGCAAAGACAAAGTAAGT
      (SEQ ID NO: 45)

3-B   AGAGTGTATCTGGCCACTGATGACCCTTCTTTT----GTTAAAGGAGGCAAAGACAAAGTAAGT
      (SEQ ID NO: 46)

4     AGAGTGTATCTGGCCACTGATGACCCTTCTTT--------AAAGGAGGCAAAGACAAAGTAAGT
      (SEQ ID NO: 47)

5     AGAGTGNATCTGGCCACTGATGACCCTTCTTT--------AAAGGAGGCAAAGACAANNNANGN
      (SEQ ID NO: 48)

6     AGAGTGTATCTGGCCACTGATGA---------------------------GACAAAGTAAGT
      (SEQ ID NO: 49)

7-A   AGAGTGTATCTGGCCACTGATGACCCTTCT-------GTTAAAGGAGGCAAAGACAAAGTAAGT
      (SEQ ID NO: 50)

7-B   AGAGTGTATCTGGCCACTGATGACCCTTCTTT---------AAGGAGGCAAAGACAAAGTAAGT
      (SEQ ID NO: 51)

8     AGAGTGTATCNGGCCACTGATGACCCTTCTTT--------AAAGGAGGCAAAGACNNAGNAAGT
      (SEQ ID NO: 52)

9     AGAGTGTATCTGGCCACTGATGACCCTTCTTT--------AAAGGAGGCAAAGACAAAGTAAGT
      (SEQ ID NO: 53)

10-A  AGAGTGTATCTG---------------------------------AGCAAAGACAAAGTAAGT
      (SEQ ID NO: 54)

10-B  AGAGTGTATCTGGCCACTG--------------------AAAGGAGGCAAAGACAAAGTAAGT
      (SEQ ID NO: 55)

11-A  AGAGTGTATCTGGCCACTGATGACCCTTCTTTGTT---ATAAAGGAGGCAAAGACAAAGTAAGT
      (SEQ ID NO: 56)

11-B  AGAGTGTATCTGGCCACTGATGACCCTT-----------TAA-GGAGGCAAAGACAAAGTAAGT
      (SEQ ID NO: 57)

12-A  AGAGTGTATCTGGCCACTGATGACCCTTCTTTGTTATGGTAAAGGAGGCAAAGACAAAGTAAGT
      (SEQ ID NO: 58)

12-B  AGAGTGTATCTGGCCACTGAT------(148bp)-----TAAAGGAGGCAAAGACAAAGTAAGT
      (SEQ ID NO: 59)

13-A  AGAGTGTATCTGGCCACTGATGACCCTT--------------------------AGTAAGT
      (SEQ ID NO: 60)

13-B  AGAGTGTATCTGGCCACTGA----------------------------------------T
      (SEQ ID NO: 61)

14-A  AGAGTGTATCTGGCCACTGATGACCCTTCTTTGTTATGTTAAAGGAGGCAAAGACAAAGTAAGT
      (SEQ ID NO: 62)

14-B  AGAGTGTATCTGGCCACTGATGACCCTTCTTTGTT---ATAAAGGAGGCAAAGACAAAGTAAGT
      (SEQ ID NO: 63)

15    AGAGTGTATCTGGCCACTGATGACCCTTCTTT--------AAAGGAGGCNAAGACAGAGTANGT
      (SEQ ID NO: 64)

For all clones sequenced, both alleles of FUT8 were modified. Five of the clones were homozygous. Genotyping also revealed clones with deletions of between 2 and 38 base pairs and small insertions of 1 to 5 base pairs. Allele B of clone 12

Example 4

Disruption of FUT8 Via Dual-ZFN-Modification

A larger deletion in FUT8 (1300 bp of FUT8, including the majority of exon 10) was also created by simultaneous transfection of the intronic ZFN pair ZFN 12029/12030 and the exonic pair ZFN 12172/12176. In particular, one microgram each of ZFNs 12029, 12030, 12172, and 12176 were transfected into CHO K-I cells as described above. Cells were harvested 2 days post-transfection and the genomic DNA purified. The DNA was digested with EcoR I and Xmn I to destroy the wild-type chromosomes and PCR amplified with the oligos GJC 71F:

```
                                       (SEQ ID NO: 4)
    GCTTGGCTTCAAACATCCAG
    and GJC 91R:

(SEQ ID NO: 7)
    TGTTACTTAAGCCCCAGGC.
```

Results are shown in FIG. 6A and demonstrate that a fragment of the expected size was generated.

CHO cell lines were also treated subsequently with different pairs of ZFNs that target the FUT8 gene with or without LCA enrichment. The CEL-I assay was performed 2 and 30 days post-transfection with ZFN plasmids as described above in Example 2.

As shown in FIG. 6B, LCA treatment resulted in significant increase in the percentage of FUT8-/- cells.

Example 5

Inactivation of Additional Genes

Cell lines were also created in which FUT8 and additional genes were inactivated. In particular, zinc finger nucleases directed to DHFR and GS were designed and constructed as described in U.S. Patent Publication Nos. 2006/0063231 and U.S. 2008/015164. Plasmids encoding DHFR- and GS-targeted ZFNs were introduced into CHO cells as described in Example 2 to create $GS^{-/-}/DHFR^{-/-}$ CHO cell line.

Figure 7:
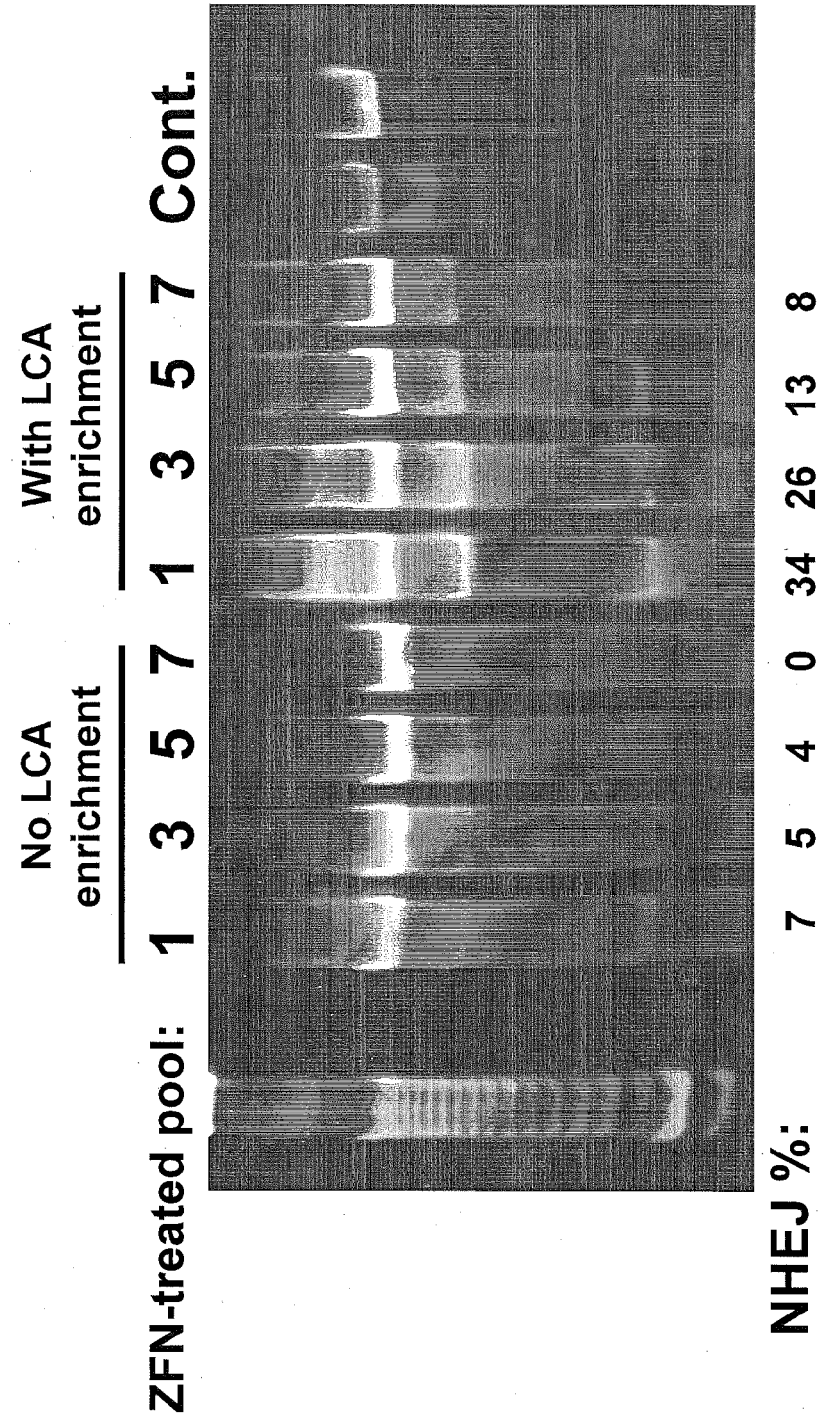
FIG. 7 shows results of Cel-1 mismatch assays for ZFN activity at the endogenous FUT8 locus with and without $Lens\ culinaris$ agglutinin (LCA) enrichment in CHO cells in which both the dihydrofolate reductase (DHFR) and glutamine synthetase (GS) genes have been disrupted by previous ZFN treatment. ZFN pools (1, 3, 5, 7) used are shown at the top of each lane and the percent of chromosomes modified by non-homologous end joining is listed below each lane. The two lanes marked "Cont." show negative controls in which cells were transfected with a GFP expression plasmid (left "Cont." lane) or untransfected (right "Cont." lane).

The $GS^{-/-}/DHFR^{-/-}$ CHO cell lines were subsequently treated with either of four different pairs of ZFNs that target the FUT8 gene (pools 1, 3, 5, and 7). Each pool was subjected to LCA to select for the population in which FUT8 expression had been destroyed (FIG. 7, With LCA enrichment). The CEL-I assay was performed on both the LCA-selected and unselected (FIG. 7, no LCA enrichment) pools as described above.

As shown in FIG. 7, the frequency of disrupted copies of the FUT8 gene in LCA-selected pools was as high as 34% (pool 1 with LCA enrichment).

Figure 8:
FIG. 8 shows the indicated characteristics of triple gene (DHFR/GS/FUT8) knockout clones isolated from LCA-enriched ZFN-treated pools #1.

Genotyping analysis of the various triple knockout clones isolated from pool #1 or pool #5 was also performed, essentially as described in Example 3 above. As shown in FIG. 8, of the 75 clones screened from pool #1, 33 (or ~44%) were modified at both copies of the FUT8 gene.

Figure 9:
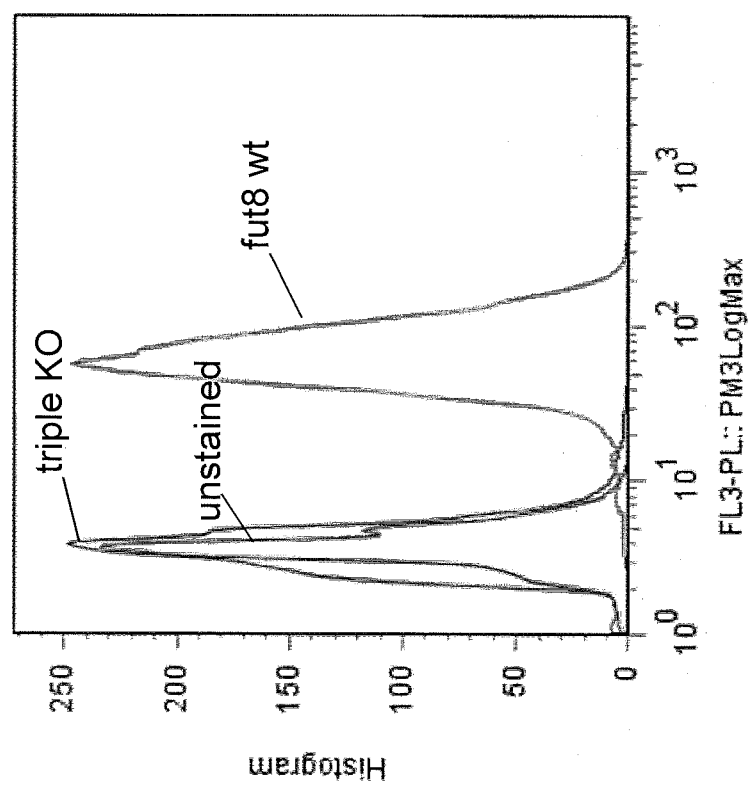
FIG. 9 is a graph depicting binding of fluorescent LCA to the indicated cell types. "Unstained" refers to CHO cells that contain wild type Fut8 but which have not been exposed to fluorescent LCA; "triple KO" refers to cells in which all three of the DHFR, GS and FUT8 genes have been disrupted using ZFNs; and "fut8 wt" refers to CHO cells that contain wild type FUT8 and have been exposed to fluorescent LCA.

Finally, CHO cells in which DHFR, GS and FUT8 were disrupted by treatment with ZFNs were also tested for their ability to bind fluorescent LCA. Approximately 100,000 cells were trypsinized, washed in 1×PBS, and mixed with 2 μg/mL fluorescein-LCA (F-LCA). F-LCA binding was assayed by flow cytometery (Yamane-Ohnuki et al. (2004) *Biotech. Bioeng.* 87:614). As shown in FIG. 9, fluorescent LCA does not bind to cells in which GS, DHFR and FUT8 genes are disrupted. Thus, cells in which any of FUT8 and one, two (or more) genes are inactivated are used for expression (overexpression) of recombinant proteins of interest.

These results show the rapid generation of Fut8-deficient cell lines using ZFNs targeted to cleave the FUT8 gene. DNA repair through the error-prone process of NHEJ at the site of cleavage resulted in functionally deleterious mutations. Although NHEJ-derived mutations are sometimes small relative to those made by conventional gene disruption, the ability of ZFNs described herein to target these mutations to the DNA coding for the critical catalytic region of FUT8 ensured that even small, in-frame alleles would result in severe defects in enzyme activity. For example, homozygous deletion of only leucine 413 (clones 5, 8, 9, and 15) resulted in cells resistant to LCA.

Furthermore, although many different subtypes of CHO cell lines exist, often with custom-made genetic or phenotypic changes, the ZFNs described herein can be used to rapidly disrupt FUT8 in any cell line or subtype. In addition, because zinc finger protein binding sites can be selected that are conserved between mammalian species, ZFNs can be designed to inactive FUT8 in cells lines derived from any species.

Example 6

Fut8 Hypomorphs

Some CHO cells with ZFN modification of FUT8 may retain a fraction of their wild-type Fut8 activity. Such cells might be resistant to the relatively low concentration of LCA used to perform the initial screen (50 μg/mL) but remain sensitive to higher concentrations of LCA.

Figure 10:
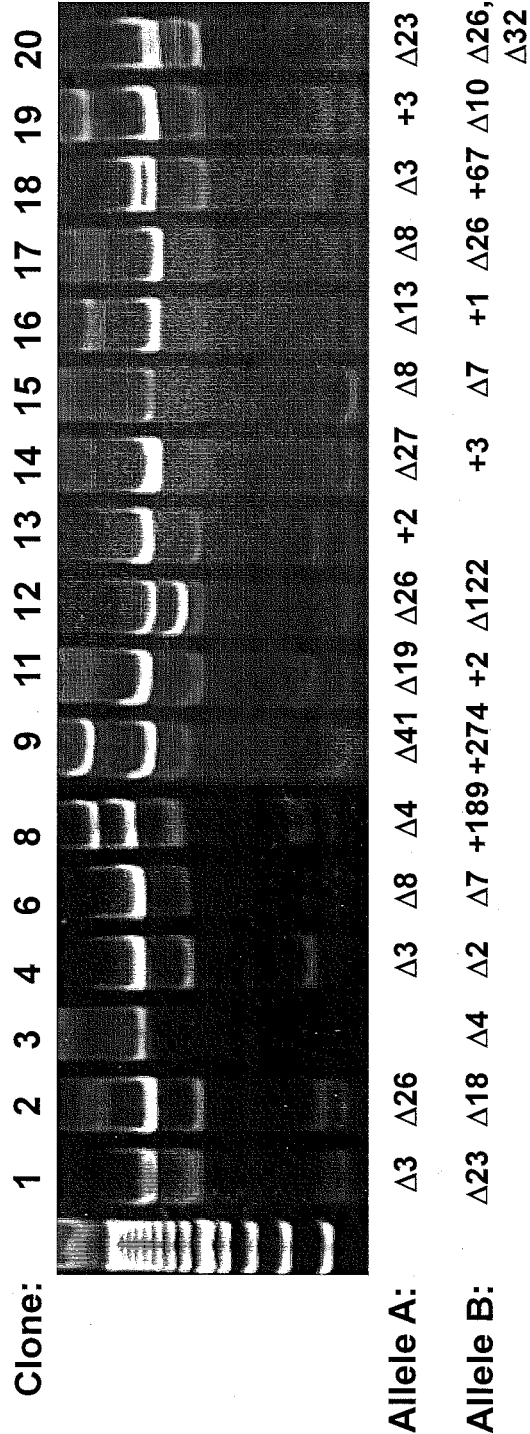
FIG. 10 shows results of Cel-1 mismatch assays for ZFN activity at the endogenous FUT8 locus in FUT8 hypomorphs. Clone number is indicated above the lane and allele disruptions are indicated below each lane.

Cells were transfected as described in Example 2 and screened for resistance to 50 μg/mL LCA and genotyped as in Example 3. A CEL-I assay of individual clones and the genotypes of some of these clones are shown in FIG. 10. After this primary screen with 50 μg/mL LCA, a secondary screen of these initial ZFN-modified LCA-resistant cell lines with higher concentrations of LCA was performed to identify hypomorphs. Cell lines resistant to 50 μg/mL LCA were assayed for growth in 100, 200, 400, and 800 μg/mL LCA. Eleven of the 16 cell lines tested in this manner exhibited wild-type growth and cell morphology at 800 μg/mL LCA. Five of the 16 cell lines tested exhibited wild-type growth and cell morphology only at LCA concentrations below 800 μg/mL These five clones with intermediate LCA resistance are therefore hypomorphic for Fut8 activity. Fut8 hypomorphism perfectly correlated with the presence of a three nucleotide (ATT) insertion between the ZFN binding sites. This insertion adds one leucine residue to the *C. griseus* Fut8 protein at position 415. The other allele in each of these clones is predicted to eliminate enzyme activity. Two of these five clones are clone 14 and clone 19 and are shown in FIG. 10.

Figure 11:
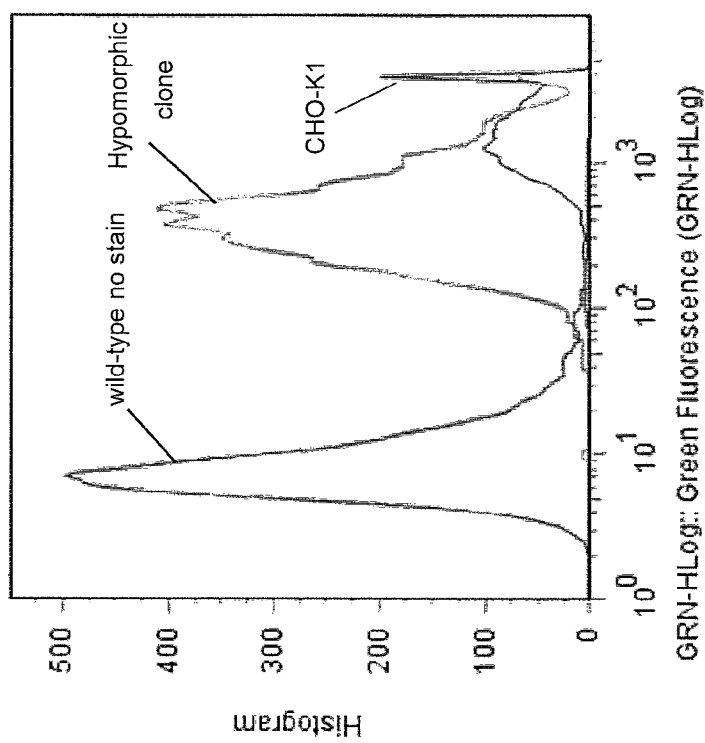
FIG. 11 is a graph depicting binding of fluorescent LCA to the indicated cell types. "Wild type no stain" refers to CHO cells that contain wild type Fut8 but which have not been exposed to fluorescent LCA; "Hypomorphic clone" refers to a population of cells in which FUT8 was partially inactivated (FUT8 hypomorph); and "CHO-K1" refers to CHO cells that contain wild type FUT8 and have been exposed to fluorescent LCA.

The hypomorphs discovered in the LCA-resistance titration were confirmed by assay of fluorescent-LCA (F-LCA) binding to cell surface-exposed α1-6-linked fucose. For each cell line analyzed approximately 100,000 cells were trypsinized, washed in 1×PBS, and mixed with 2 μg/mL fluorescein-LCA (F-LCA). F-LCA binding was assayed by flow cytometry (Guava Technologies). All of the hypomorphic clones examined by F-LCA binding had ~5-fold less F-LCA binding than wild-type; all clones resistant to 800 μg/mL LCA showed no ability to bind F-LCA. Staining of wild-type CHO-KI cells and one such hypomorphic clone is shown in FIG. 11.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of inactivating an endogenous cellular FUT8 gene in an isolated cell, the method comprising:

introducing, into an isolated cell, a first nucleic acid encoding a first polypeptide, wherein the first polypeptide comprises:

(a) a first zinc finger DNA-binding domain, wherein the DNA-binding domain comprises four or five zinc finger recognition regions ordered F1 to F4, F1 to F5 or F1 to F6 from N-terminus to C-terminus, and wherein F1 to F4, F1 to F5 or F1 to F6 comprise amino acid sequences selected from the group consisting of:

```
(i)      F1: QSSDLSR (SEQ ID NO: 9);
         F2: TSGNLTR (SEQ ID NO: 10);
         F3: RSDDLSK (SEQ ID NO: 11);
         and
         F4: DRSALAR (SEQ ID NO: 12);

(ii)     F1: RSDVLSA (SEQ ID NO: 14);
         F2: QNATRIN (SEQ ID NO: 15);
         F3: DRSNLSR (SEQ ID NO: 16);
         and
         F4: RLDNRTA (SEQ ID NO: 17);

(iii)    F1: RSDNLRE (SEQ ID NO: 26);
         F2: NNTQLIE (SEQ ID NO: 27);
         F3: TSSILSR (SEQ ID NO: 28);
         F4  RSDNLSA (SEQ ID NO: 29);
         and
         F5: RKDTRIT (SEQ ID NO: 30);
         and (iv)     F1: RSDNLSV (SEQ ID NO: 19);
         F2: QNATRIN (SEQ ID NO: 15);
         F3: RSDNLST (SEQ ID NO: 20)
         or RSDHLSQ (SEQ ID NO: 24);
         F4: QSATRTK (SEQ ID NO: 21);
         F5 RSDNLSR (SEQ ID NO: 22);
         and
         F6: RNDNRKT (SEQ ID NO: 23);
         and
```

(b) a first cleavage domain; such that the polypeptide is expressed in the cell, whereby the polypeptide binds to the target site and cleaves the FUT8 gene; and introducing a nucleic acid encoding a second polypeptide, wherein the second polypeptide comprises:

(i) a second zinc finger DNA-binding domain that is engineered to bind to a second target site in the FUT8 gene; and (ii) a second cleavage domain; such that the second polypeptide is expressed in the cell, whereby the first and second polypeptides bind to their respective target sites, dimerize and cleave the FUT8 gene, thereby inactivating the FUT8 gene.

2. The method of claim 1, wherein the first and second polypeptides are encoded by the same nucleic acid.

3. The method of claim 1, wherein the first and second polypeptides are encoded by different nucleic acids.

4. The method of claim 1, wherein the first or second cleavage domain is a wild-type FokI cleavage domain.

5. The method of claim 1, wherein the first or second cleavage domain is an engineered FokI cleavage domain.

6. The method of claim 1, further comprising introducing donor sequence into the cell such that the donor sequence is integrated into the inactivated FUT8 gene.

7. A method of producing a recombinant protein of interest in an isolated cell, the method comprising the steps of:

(a) providing an isolated cell comprising an endogenous FUT8 gene;

(b) inactivating the endogenous FUT8 gene of the isolated cell by the method of claim 1; and (c) introducing an expression vector comprising a transgene, the transgene comprising a sequence encoding a protein of interest into the cell, thereby producing the recombinant protein.

8. The method of claim 7, wherein the protein of interest comprises an antibody.

9. A cell or cell line in which Fut8 is partially or fully inactivated, wherein the cell or cell line is produced by (a) inactivating Fut8 in a cell according to the method of claim 1; and (b) culturing the cell under conditions suitable for generating a cell or cell line in which Fut8 is partially or fully inactivated.

10. The cell or cell line of claim 9, wherein the cell is a mammalian cell or cell line selected from the group consisting of a COS cell, a CHO cell, a VERO cell, a MDCK cell, a WI38 cell, a V79 cell, a B14AF28-G3 cell, a BHK cell, a HaK cell, a NS0 cell, a SP2/0-Ag14 cell, a HeLa cell, an HEK293 cell, and a perC6 cell.

11. The cell or cell line of claim 9, wherein one or more additional genes are partially or fully inactivated.

12. The cell or cell line of claim 11, wherein dihydrofolate reducatase (DHFR) and glutamine synthetase (GS) have been inactivated.

* * * * *

SEQUENCE LISTING

```
<160> NUMBER OF SEQ ID NOS: 66

<210> SEQ ID NO 1
<211> LENGTH: 1890
<212> TYPE: DNA
<213> ORGANISM: C. griseus

<400> SEQUENCE: 1
aacagaaact tattttcctg tgtggctaac tagaaccaga gtacaatgtt tccaattctt      60
tgagctccga gaagacagaa gggagttgaa actctgaaaa tgcgggcatg gactggttcc    120
tggcgttgga ttatgctcat tcttttttgcc tgggggaccct tattgtttta tataggtggt    180
catttggttc gagataatga ccaccctgac cattctagca gagaactctc caagattctt    240
gcaaagctgg agcgcttaaa acaacaaaat gaagacttga ggagaatggc tgagtctctc    300
cgaataccag aaggccctat tgatcagggg acagctacag gaagagtccg tgttttagaa    360
gaacagcttg ttaaggccaa agaacagatt gaaaattaca agaaacaagc taggaatgat    420
ctgggaaagg atcatgaaat cttaaggagg aggattgaaa atggagctaa agagctctgg    480
ttttttctac aaagtgaatt gaagaaatta aagaaattag aaggaaacga actccaaaga    540
catgcagatg aaattctttt ggatttagga catcatgaaa ggtctatcat gacagatcta    600
tactacctca gtcaaacaga tggagcaggt gagtggcggg aaaaagaagc caaagatctg    660
acagagctgg tccagcggag aataacatat ctgcagaatc ccaaggactg cagcaaagcc    720
agaaagctgg tatgtaatat caacaaaggc tgtggctatg gatgtcaact ccatcatgtg    780
gtttactgct tcatgattgc ttatggcacc cagcgaacac tcatcttgga atctcagaat    840
tggcgctatg ctactggagg atgggagact gtgtttagac ctgtaagtga gacatgcaca    900
gacaggtctg gcctctccac tggacactgg tcaggtgaag tgaaggacaa aaatgttcaa    960
gtggtcgagc tccccattgt agacagcctc catcctcgtc ctccttactt acccttggct   1020
gtaccagaag accttgcaga tcgactcctg agagtccatg gtgatcctgc agtgtggtgg   1080
gtatcccagt ttgtcaaata cttgatccgt ccacaacctt ggctggaaag ggaaatagaa   1140
gaaaccacca agaagcttgg cttcaaacat ccagttattg gagtccatgt cagacgcact   1200
gacaaagtgg gaacagaagc agccttccat cccattgagg aatacatggt acacgttgaa   1260 gaacatttc agcttctcga acgcagaatg aaagtggata aaaaaagagt gtatctggcc   1320
actgatgacc cttctttgtt aaaggaggca aagacaaagt actccaatta tgaatttatt   1380
agtgataact ctatttcttg gtcagctgga ctacacaacc gatacacaga aaattcactt   1440
cggggcgtga tcctggatat acactttctc tcccaggctg acttccttgt gtgtactttt   1500
tcatcccagg tctgtagggt tgcttatgaa atcatgcaaa cactgcatcc tgatgcctct   1560
gcaaacttcc attctttaga tgacatctac tattttggag gccaaaatgc ccacaaccag   1620
attgcagttt atcctcacca acctcgaact aaagaggaaa tccccatgga acctggagat   1680
atcattggtg tggctggaaa ccattggaat ggttactcta aaggtgtcaa cagaaaacta   1740
ggaaaaacag gcctgtaccc ttcctacaaa gtccgagaga agatagaaac agtcaaatac   1800
cctacatatc ctgaagctga aaaatagaga tggagtgtaa gagattaaca acagaattta   1860
```

-continued

```
gttcagacca tctcagccaa gcagaagacc                                          1890
```

<210> SEQ ID NO 2
<211> LENGTH: 575
<212> TYPE: PRT
<213> ORGANISM: C. griseus

<400> SEQUENCE: 2

```
Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Asp Leu Gly Lys Asp His
            100                 105                 110

Glu Ile Leu Arg Arg Ile Glu Asn Gly Ala Lys Glu Leu Trp Phe
        115                 120                 125

Phe Leu Gln Ser Glu Leu Lys Lys Leu Lys Lys Leu Glu Gly Asn Glu
130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Glu Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
    210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Lys Asp Lys Asn Val Gln Val
        275                 280                 285

Val Glu Leu Pro Ile Val Asp Ser Leu His Pro Arg Pro Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Arg Glu Ile Glu Glu Thr Thr Lys Lys
            340                 345                 350

Leu Gly Phe Lys His Pro Val Ile Gly Val His Val Arg Arg Thr Asp
        355                 360                 365
```

```
Lys Val Gly Thr Glu Ala Ala Phe His Pro Ile Glu Glu Tyr Met Val
            370                 375                 380

His Val Glu Glu His Phe Gln Leu Leu Glu Arg Arg Met Lys Val Asp
385                 390                 395                 400

Lys Lys Arg Val Tyr Leu Ala Thr Asp Asp Pro Ser Leu Leu Lys Glu
                405                 410                 415

Ala Lys Thr Lys Tyr Ser Asn Tyr Glu Phe Ile Ser Asp Asn Ser Ile
                420                 425                 430

Ser Trp Ser Ala Gly Leu His Asn Arg Tyr Thr Glu Asn Ser Leu Arg
            435                 440                 445

Gly Val Ile Leu Asp Ile His Phe Leu Ser Gln Ala Asp Phe Leu Val
450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
            500                 505                 510

His Gln Pro Arg Thr Lys Glu Glu Ile Pro Met Glu Pro Gly Asp Ile
            515                 520                 525

Ile Gly Val Ala Gly Asn His Trp Asn Gly Tyr Ser Lys Gly Val Asn
530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 3
<211> LENGTH: 2104
<212> TYPE: DNA
<213> ORGANISM: C. griseus

<400> SEQUENCE: 3
aggtgaagtg aaggacaaaa atgttcaagt ggtcgagctc cccattgtag acagcctcca    60
tcctcgtcct ccttacttac ccttggctgt accagaagac cttgcagatc gactcctgag   120
agtccatggt gatcctgcag tgtggtgggt atcccagttt gtcaaatact tgatccgtcc   180
acaaccttgg ctggaaaggg aaatagaaga aaccaccaag aagcttggct tcaaacatcc   240
agttattggg taagaatcta tcccctccc cttaaacagt aatatatagc agtagttgta   300
tgtgtttact ttttactgta gatttttataa tatttaatag tcatagtccc accaaagaac   360
aaagattcta aaacttaaaa gactattctc cctttgttca gttagggcag cagagcaaat   420
ggtgcagtgt gtccttctgc tgtctcggat gctcttcttc ctttcatttt ttatgaagct   480
ccttggtttt atttttatat ttcctattcc acaaatttct tcatctctta atctttatat   540
gtagagttgt tactgacccc tcttctaaat gttagaggta acgaaagtac atagtgaaac   600
cagaatatta aatagtgttc atctcctcag acttcattga aattcagtgt ggcacattct   660
ccctgcctca cttcatttgt atagaacaca cggaacaagt ccaatttcct gagagaaaca   720
gtgattaaga ggaatgtagg aaagaaaaga tgactgcata gttattcctg tggtcaaatc   780
cacaactgga ctatagtctg ggatgcaaag gaaacagtag catgaaggtg gcacagttac   840
cccagtgtgc tacagccctg actccagatt caagacataa ccctgtcttt ggcaacacta   900
agatgcagga gagtgctggg aagtcagtga cttggccatt gcaggtcagt gtaagtctgt   960
```

```
attccttgct ttataacatt gtgacttttc ttcaaaatga gaaaatgagg tctgtttctg   1020
tttgcagttg atagagaaaa aaaatgcaaa aaaagtctgt agtaacttca tgaacataaa   1080
ataaccaaca tctttaaaag gctagcttgt cttaaactac aggaaaagtt catatggatc   1140
tttgttttct tagatgactt taaattctat gaactgaagt ggtagtaact ttacagggta   1200
aaatgaaaga aaaaaattaa taaactttgg cataagaatg ttacaagcat tatctttaag   1260 cttttgaattc tgttatgatt ttggtctcaa aaaccaaaaa acttaaatct gttgattcca   1320
ggttcccata tattcttgga tatgccaatt acttttttctg taagcaagtg tttcataaaa   1380
cttttactta actttcatat tgacctgtac tattcaacat tcagctatgt taaagtattt   1440
gtgaagtgtt ttgaaatgat tttatatttt ctaaggtgag aataaatgag aaaatgtttt   1500
aatatgtctc cagtgccccc atgactaggg atactaattg agtaccagta cattatcagt   1560
gtgctctcca cttctcccca gagtccatgt cagacgcact gacaaagtgg aacagaagc    1620 agccttccat cccattgagg aatacatggt acacgttgaa gaacattttc agcttctcga   1680
acgcagaatg aaagtggata aaaaagagt gtatctggcc actgatgacc cttctttgtt   1740
aaaggaggca aagacaaagt aagttagacc aacaagtggt tctgtatggg attatctctt   1800
agttgaagaa aatccttaat tctgggaact tgtggttctt gttgctaact aataggttcc   1860
aaaatcaaag actacatgtg caaatattaa tctaatcaag tcataccttta ctagctgtat   1920 ctgatgcaaa ttaagaagtc taaaatgaat tagactgctg atttgtgtag catcactagc   1980
agtcatcatt caacacagta ccacacttct tagtaccaaa atctgtttaa catactagag   2040
tttccataaa tcaaattttg tagcctgggg cttaagtaac agaagtttat gtctcacagt   2100
tctg                                                               2104

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
gcttggcttc aaacatccag                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ggacttgttc cgtgtgttct                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
ctgttgattc caggttccca                                              20

<210> SEQ ID NO 7
<211> LENGTH: 19
```

```
<212> TYPE: DNA
<213> ORGANISM: Artificial Sequence
<220> FEATURE:
<223> OTHER INFORMATION: Synthetic oligonucleotide

<400> SEQUENCE: 7
tgttacttaa gccccaggc                                                  19

<210> SEQ ID NO 8
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 8
gtctcggatg ct                                                         12

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Gln Ser Ser Asp Leu Ser Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Thr Ser Gly Asn Leu Thr Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Arg Ser Asp Asp Leu Ser Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Asp Arg Ser Ala Leu Ala Arg
1               5

<210> SEQ ID NO 13
<211> LENGTH: 12
<212> TYPE: DNA
<213> ORGANISM: Artificial Sequence
<220> FEATURE:
```

<223> OTHER INFORMATION: Synthetic oligonucleotide

<400> SEQUENCE: 13
aaggacacac tg                                                              12

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Arg Ser Asp Val Leu Ser Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Gln Asn Ala Thr Arg Ile Asn
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Asp Arg Ser Asn Leu Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Arg Leu Asp Asn Arg Thr Ala
1               5

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 18
aaggaggcaa agacaaag                                                        18

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

```
Arg Ser Asp Asn Leu Ser Val
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Arg Ser Asp Asn Leu Ser Thr
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Gln Ser Ala Thr Arg Thr Lys
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Arg Ser Asp Asn Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Arg Asn Asp Asn Arg Lys Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Arg Ser Asp His Leu Ser Gln
1               5

<210> SEQ ID NO 25
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 25
```
aagaagggtc atcag                                                15

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Arg Ser Asp Asn Leu Arg Glu
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Asn Asn Thr Gln Leu Ile Glu
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide

<400> SEQUENCE: 28

Thr Ser Ser Ile Leu Ser Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29

Arg Ser Asp Asn Leu Ser Ala
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Arg Lys Asp Thr Arg Ile Thr
1               5

<210> SEQ ID NO 31
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 31
aacagaaact tattttcctg tgt                                       23

-continued

```
<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
ggtcttctgc ttggctgaga                                                  20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
cactttgtca gtgcgtctga                                                  20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
agtccatgtc agacgcactg                                                  20

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
cagaactgtg agacataaac tg                                               22

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide

<400> SEQUENCE: 36

Thr Gly Glu Lys Pro
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide

<400> SEQUENCE: 37

Thr Gly Gly Gln Arg Pro
1               5

<210> SEQ ID NO 38
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 38

Thr Gly Gln Lys Pro
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide

<400> SEQUENCE: 39

Thr Gly Ser Gln Lys Pro
1               5

<210> SEQ ID NO 40
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 40
agagtgtatc tggccactga tgacccttct ttgttaaagg aggcaaagac aaagtaagt      59

<210> SEQ ID NO 41
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 41
agagtgtatc tggccactga tgacccttta aggaggcaaa gacaaagtaa gt             52

<210> SEQ ID NO 42
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 42
agagtgtatc tggccactga tgacccttct ttgttataaa ggaggcaaag acaaagtaag     60
t                                                                     61

<210> SEQ ID NO 43
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 43
agagtgtatc tggccactga aagacaaagt aagt                                 34

<210> SEQ ID NO 44
<211> LENGTH: 52
<212> TYPE: DNA
<213> ORGANISM: Artificial Sequence
<220> FEATURE:
<223> OTHER INFORMATION: Synthetic oligonucleotide
```

<400> SEQUENCE: 44
agagtgtatc tggccactga tgaccgttaa aggaggcaaa gacaaagtaa gt    52

<210> SEQ ID NO 45
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 45
agagtgtatc tggccactga tgacccttct ttgttatgtt aaaggaggca aagacaaagt    60
aagt    64

<210> SEQ ID NO 46
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 46
agagtgtatc tggccactga tgacccttct tttgttaaag gaggcaaaga caaagtaagt    60

<210> SEQ ID NO 47
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 47
agagtgtatc tggccactga tgacccttct ttaaaggagg caaagacaaa gtaagt    56

<210> SEQ ID NO 48
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (50)..(52)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t

<400> SEQUENCE: 48
agagtgnatc tggccactga tgacccttct ttaaaggagg caaagacaan nnangn    56

<210> SEQ ID NO 49
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 49

```
agagtgtatc tggccactga tgagacaaag taagt                                  35

<210> SEQ ID NO 50
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 50
agagtgtatc tggccactga tgacccttct gttaaaggag gcaaagacaa agtaagt         57

<210> SEQ ID NO 51
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 51
agagtgtatc tggccactga tgacccttct ttaaggaggc aaagacaaag taagt           55

<210> SEQ ID NO 52
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 52
agagtgtatc nggccactga tgacccttct ttaaggagg caaagacnna gnaagt            56

<210> SEQ ID NO 53
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 53
agagtgtatc tggccactga tgacccttct ttaaggagg caaagacaaa gtaagt            56

<210> SEQ ID NO 54
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 54
agagtgtatc tgagcaaaga caaagtaagt                                        30

<210> SEQ ID NO 55
<211> LENGTH: 43
<212> TYPE: DNA
```

```
<213> ORGANISM: Artificial Sequence
<220> FEATURE:
<223> OTHER INFORMATION: Synthetic oligonucleotide

<400> SEQUENCE: 55
agagtgtatc tggccactga aaggaggcaa agacaaagta agt                   43

<210> SEQ ID NO 56
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 56
agagtgtatc tggccactga tgacccttct ttgttataaa ggaggcaaag acaaagtaag   60
t                                                                  61

<210> SEQ ID NO 57
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 57
agagtgtatc tggccactga tgacccttta aggaggcaaa gacaaagtaa gt          52

<210> SEQ ID NO 58
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 58
agagtgtatc tggccactga tgacccttct ttgttatggt aaaggaggca agacaaagt   60 aagt                                                               64

<210> SEQ ID NO 59
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 59
agagtgtatc tggccactga ttaaaggagg caaagacaaa gtaagt                 46

<210> SEQ ID NO 60
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 60
agagtgtatc tggccactga tgacccttag taagt                             35

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 61
agagtgtatc tggccactga t                                              21

<210> SEQ ID NO 62
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 62
agagtgtatc tggccactga tgacccttct ttgttatgtt aaaggaggca agacaaagt     60 aagt                                                                 64

<210> SEQ ID NO 63
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 63
agagtgtatc tggccactga tgacccttct ttgttataaa ggaggcaaag acaaagtaag    60
t                                                                    61

<210> SEQ ID NO 64
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t

<400> SEQUENCE: 64
agagtgtatc tggccactga tgacccttct ttaaaggagg cnaagacaga gtangt        56

<210> SEQ ID NO 65
<211> LENGTH: 14
<212> TYPE: PRT
<213> ORGANISM: Artificial Sequence
<220> FEATURE:
<223> OTHER INFORMATION: Synthetic peptide

<400> SEQUENCE: 65

Arg Val Tyr Leu Ala Thr Asp Asp Pro Ser Leu Leu Lys Glu
1               5                   10

<210> SEQ ID NO 66
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 66
agagtgtatc tggccactga tgacccttct ttgttaaagg aggcaaagac aaagt         55
```